US012605552B2

(12) United States Patent
Dinsmoor et al.

(10) Patent No.:  US 12,605,552 B2
(45) Date of Patent:       Apr. 21, 2026

(54) INDEPENDENT MODULATION OF STIMULATION THERAPY WAVEFORMS

(71) Applicant: Medtronic, Inc., Minneapolis, MN (US)

(72) Inventors: David A. Dinsmoor, North Oaks, MN (US); Leonid M. Litvak, Bet Shemesh (IL); Jeffery M. Kramer, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 293 days.

(21) Appl. No.: 18/546,907

(22) PCT Filed: Feb. 22, 2022

(86) PCT No.: PCT/US2022/017309
§ 371 (c)(1),
(2) Date: Aug. 17, 2023

(87) PCT Pub. No.: WO2022/182656
PCT Pub. Date: Sep. 1, 2022

(65) Prior Publication Data
US 2024/0139521 A1      May 2, 2024

Related U.S. Application Data

(60) Provisional application No. 63/152,965, filed on Feb. 24, 2021.

(51) Int. Cl.
*A61N 1/36*          (2006.01)
*A61B 5/00*          (2006.01)
*A61B 5/388*         (2021.01)

(52) U.S. Cl.
CPC .......... *A61N 1/36178* (2013.01); *A61B 5/388* (2021.01); *A61B 5/4836* (2013.01); *A61N 1/36139* (2013.01); *A61N 1/36171* (2013.01)

(58) Field of Classification Search
CPC ........................... A61N 1/36178; A61B 5/388
(Continued)

(56) References Cited

U.S. PATENT DOCUMENTS

2013/0282078 A1*  10/2013  Wacnik ................ A61N 1/3615
607/59
2016/0082252 A1    3/2016  Hershey et al.
(Continued)

OTHER PUBLICATIONS

International Preliminary Report on Patentability from International Application No. PCT/US2022/017309 dated Sep. 7, 2023, 7 pp.
(Continued)

*Primary Examiner* — Nadia A Mahmood
(74) *Attorney, Agent, or Firm* — Shumaker & Sieffert, P.A.

(57) ABSTRACT

Devices, systems, and techniques are configured for independently modulating two or more concurrent signals of electrical stimulation therapy. In one example, a system includes stimulation generation circuitry and processing circuitry configured to control the stimulation generation circuitry to deliver first electrical stimulation to a patient via a first electrode combination, wherein the first electrical stimulation is defined by at least a first set of stimulation parameters selected that the first electrical stimulation exceeds a first perception threshold, and control the stimulation generation circuitry to deliver second electrical stimulation, concurrent with the first electrical stimulation, to the patient via a second electrode combination. The second electrical stimulation may be defined by at least a second set of stimulation parameters selected that the second electrical stimulation is below a second perception threshold. The processing circuitry may also determine a triggering condition and independently modulate the first and/or second electrical stimulation.

25 Claims, 8 Drawing Sheets

(58) Field of Classification Search
USPC .......................................................... 607/59
See application file for complete search history.

(56) References Cited

U.S. PATENT DOCUMENTS

| | | |
|---|---|---|
| 2020/0101284 A1 | 4/2020 | Marnfeldt et al. |
| 2020/0147391 A1 | 5/2020 | Moffitt |

OTHER PUBLICATIONS

International Search Report and Written Opinion of International Application No. PCT/US2022/017309, dated Jun. 8, 2022, 10 pp.

\* cited by examiner

300

INDEPENDENT MODULATION OF STIMULATION THERAPY WAVEFORMS

This application is a national stage entry of International Patent Application No. PCT/US2022/017309, filed Feb. 22, 2022, which claims priority to and the benefit of U.S. Provisional Patent Application No. 63/152,965, filed Feb. 24, 2021, the entire contents of application nos. PCT/US2022/017309 and 63/152,965 which are incorporated herein by reference.

TECHNICAL FIELD

This disclosure generally relates to electrical stimulation therapy.

BACKGROUND

Medical devices may be external or implanted and may be used to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively.

Electrical stimulation may be delivered to a patient by the medical device in a train of electrical stimulation pulses, and parameters of the electrical pulses may include a frequency, an amplitude, a pulse width, and a pulse shape. An evoked compound action potential (ECAP) is synchronous firing of a population of neurons which occurs in response to the application of a stimulus including, in some cases, an electrical stimulus by a medical device. The ECAP may be detectable as being a separate event from the stimulus itself, and the ECAP may reveal characteristics of the effect of the stimulus on the nerve fibers.

SUMMARY

In general, systems, devices, and techniques are described for independently modulating or otherwise controlling each stimulation waveform of a plurality of electrical stimulation waveforms delivered to a patient concurrently (e.g., simultaneously, interleaved, and/or on an intermittent basis). More specifically, the systems described herein are configured to determine a predetermined set of triggering criteria or conditions, and then independently modulate each stimulation waveform of two or more stimulation waveforms in response to determining the criteria or conditions. Such independent modulation may enable a system to maintain patient comfort, improve patient outcomes, improve management of resources, or achieve any of a number of other similar practical applications and benefits.

Devices and systems described herein may include an implantable medical device (IMD) and/or programmer device configured to independently manage two or more concurrent stimulation waveforms, such as by modifying only one of the waveforms, or by modifying both of the waveforms according to different therapy-waveform-modulation programs, in response to the presence or absence of a triggering condition. As used herein, a stimulation "waveform" may include a "train" of discrete stimulation pulses, a continuous electrical signal of varying amplitude, or a combination thereof, for example, applied via a common electrode combination. In some examples (but not all examples) described herein, one waveform of the plurality of waveforms may be a "perceptible" waveform (e.g., electrical stimulation that produces an effect that may be perceived by the patient because the stimulation exceeds a first perception threshold) and another waveform of the plurality of waveforms may be an "imperceptible" waveform (e.g., electrical stimulation that is below a second perception threshold, such that it does not produce an effect perceivable by the patient). In such examples, the techniques described herein include selectively modulating either or both of the waveforms independently from each other to maintain or even improve therapeutic effects for the patient in certain predetermined scenarios.

In one example, this disclosure describes a medical device system that includes: stimulation generation circuitry configured to generate first electrical stimulation and generate second electrical stimulation at least partially concurrent with the first electrical stimulation; and processing circuitry configured to: control the stimulation generation circuitry to deliver the first electrical stimulation to a patient via a first electrode combination, wherein the first electrical stimulation is defined by at least a first set of stimulation parameters selected that the first electrical stimulation exceeds a first perception threshold; control the stimulation generation circuitry to deliver the second electrical stimulation to the patient via a second electrode combination, wherein the second electrical stimulation is defined by at least a second set of stimulation parameters selected that the second electrical stimulation is below a second perception threshold; determine a triggering condition; and responsive to determining the triggering condition, independently modulate one of the first electrical stimulation or the second electrical stimulation.

In some examples, a method includes: generating, by stimulation generation circuitry, first electrical stimulation and generate second electrical stimulation at least partially concurrent with the first electrical stimulation; controlling, by processing circuitry, the stimulation generation circuitry to deliver the first electrical stimulation to a patient via a first electrode combination, wherein the first electrical stimulation is defined by at least a first set of stimulation parameters selected that the first electrical stimulation exceeds a first perception threshold; controlling, by the processing circuitry, the stimulation generation circuitry to deliver the second electrical stimulation to the patient via a second electrode combination, wherein the second electrical stimulation is defined by at least a second set of stimulation parameters selected that the second electrical stimulation is below a second perception threshold; determining, by the processing circuitry, a triggering condition; and responsive to determining the triggering condition, independently modulating, by the processing circuitry, one of the first electrical stimulation or the second electrical stimulation.

In some examples, a non-transitory, computer-readable medium includes instructions that, when executed, cause a processor of a medical device to: control stimulation generation circuitry to deliver first electrical stimulation to a patient via a first electrode combination, wherein the first electrical stimulation is defined by at least a first set of stimulation parameters selected that the first electrical stimulation exceeds a first perception threshold; control the stimulation generation circuitry to deliver second electrical stimulation to the patient via a second electrode combination, wherein the second electrical stimulation is defined by at least a second set of stimulation parameters selected that the second electrical stimulation is below a second perception threshold; determine a triggering condition; and responsive to determining the triggering condition, independently modulate one of the first electrical stimulation or the second electrical stimulation.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

DETAILED DESCRIPTION

Figure 1:
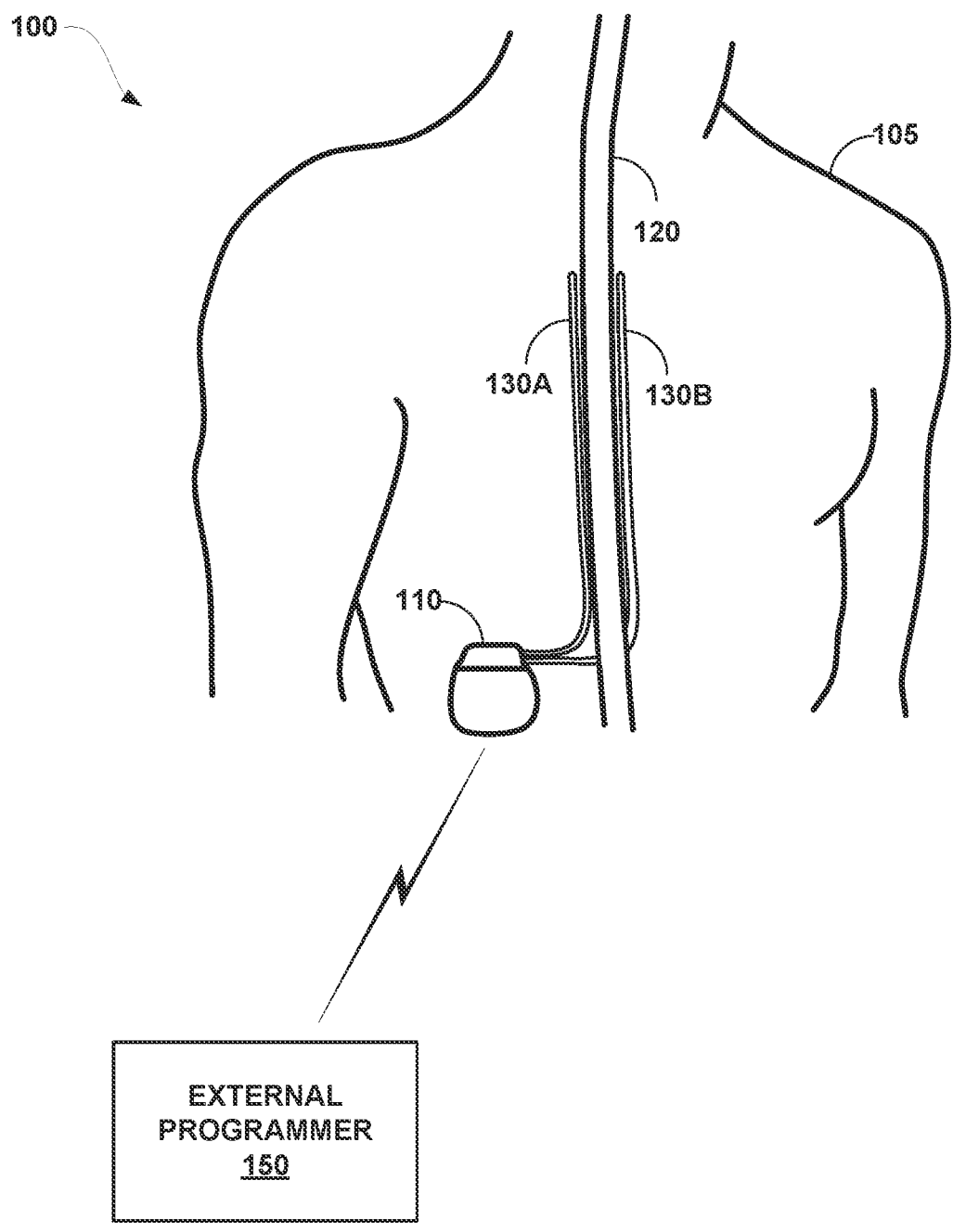
FIG. 1 is a conceptual diagram illustrating an example system that includes an implantable medical device (IMD) configured to deliver electrical stimulation therapy and an external programmer, in accordance with techniques of this disclosure.

The disclosure describes examples of medical devices, systems, and techniques for independently controlling or otherwise managing each waveform of a plurality of electrical stimulation waveforms when two or more waveforms are delivered to a patient concurrently. As used herein, a stimulation "waveform" may include a "train" of discrete stimulation pulses, a continuous electrical signal of varying amplitude, or some combination thereof, for example, applied via a single, common electrode combination. Electrical stimulation therapy is typically delivered to a target tissue (e.g., nerves of the spinal cord or muscle) of a patient via two or more electrodes. Parameters of the electrical stimulation therapy (e.g., electrode combination, voltage or current amplitude, pulse width, pulse frequency, etc.) are selected by a clinician and/or the patient to provide relief from various symptoms, such as pain, nervous system disorders, muscle disorders, etc. Various thresholds, such as a perception threshold and/or discomfort threshold to stimulation may be determined for the patient and used to select and/or recommend parameters of the stimulation therapy.

In some systems, different stimulation waveforms may be delivered to a patient concurrently as part of a comprehensive therapy program. For example, these waveforms may be directed to different symptoms, different anatomical structures that work together, or otherwise configured to operate together to provide an overall therapy to the patient. In some examples, these waveforms may be interleaved or even delivered simultaneously. When a system delivers multiple stimulation waveforms in this manner, the system may change parameters of the stimulation waveforms together in order to maintain some relationship between the waveforms. For example, the system may increase an amplitude of one waveform which causes the system to also increase the amplitude of another waveform of the therapy. However, modulating therapy in this manner prevents the system from addressing each waveform independently in order to achieve or maintain improved therapy efficacy for the patient. In addition, stimulation waveforms linked together in this manner may require unnecessary power consumption, e.g., when one of the waveforms is not needed at certain times during therapy.

As described herein, systems, devices, and techniques are described for independently controlling or otherwise managing each of a plurality of electrical stimulation waveforms when two or more waveforms are delivered to a patient concurrently. In some examples, the systems described herein are configured to determine a set of "triggering" criteria or conditions objectively defining one of several predetermined scenarios that present at least one constraint on the system. In response, the systems described herein are configured to independently manage two or more stimulation waveforms in response to determining the triggering criteria or conditions, such as to maintain patient comfort, improve patient outcomes, improve management of resources (e.g., reduce power consumption), or any of a number of other similar practical applications and benefits, while subject to the constraint.

Devices and systems described herein may include an implantable medical device (IMD) and/or programmer device configured to independently manage two or more concurrent stimulation waveforms, such as by modifying only one of the waveforms, or by modifying each of the waveforms according to different modulation programs, in response to the presence or absence of an identified triggering condition.

In some examples (but not all examples) described herein, the two or more stimulation waveforms may include both a "perceptible" waveform (e.g., electrical stimulation that produces an effect that may be perceived by the patient such as stimulation with an intensity exceeding a first perception threshold) and an "imperceptible" waveform (e.g., electrical stimulation that does not produce patient-perceivable effects or is below a second perception threshold). A perception threshold may indicate an intensity, such as one or more parameter values (e.g., at least one of a stimulation amplitude, pulse width, frequency, etc.) at which the patient can perceive the stimulation. In addition, or alternatively, the perception threshold may be associated with a sensed variable representative of a physiological response from the patient, such as an ECAP, local field potential, or other sensed signal. In some examples, the first perception threshold and the second perception threshold may be identical for different waveforms of electrical stimulation. In other examples, the first perception threshold for one waveform may be different than a second perception threshold for a different waveform. In such examples, the techniques described herein include intelligently modulating either or both of the waveforms to maintain or even improve therapeutic effects for the patient. Some specific, non-limiting, illustrative examples of triggering conditions and corresponding waveform-modulation programs are detailed below.

As one non-limiting, illustrative example, the medical device may deliver a lower-frequency (e.g., from about 40-60 Hz, or about 50 Hz) stimulation train or waveform to the patient via a first electrode combination, while concurrently delivering a higher-frequency (e.g., from about 100-1,200 Hz, or about 1000 Hz) stimulation train or waveform to the patient via a second electrode combination. The lower-frequency waveform may be configured, for example, to elicit therapeutic sensations of paresthesia in the patient. The higher-frequency waveform may be configured to modulate a neurochemical process and may not produce sensations perceivable by the patient. In other examples, the medical device may deliver more than two waveforms having different pulse widths, pulse frequencies, pulse amplitudes, waveform shapes, electrode combinations, and/ or interphase intervals. In response to determining a triggering condition such as a low battery capacity, the system may be configured to reduce the amplitude of the imperceptible waveform or even cycle the imperceptible waveform on and off over time in order to reduce power consumption while that waveform is not needed for stimulation. As another example, in response to determining a triggering condition such as changes in patient activity, the system may independently increase or decrease the amplitude of the perceptible waveform while maintaining the parameter values of the imperceptible waveform to maintain effective therapy during the changes to the patient activity. These and other examples are described further herein.

FIG. 1 is a conceptual diagram illustrating an example system 100 that includes an implantable medical device (IMD) 110 and an external programmer 150, in accordance with one or more techniques of this disclosure. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable system configured to deliver spinal cord stimulation (SCS) therapy for purposes of illustration, but without limitation as to other types of medical devices or other therapeutic applications of medical devices.

As shown in FIG. 1, system 100 includes an IMD 110, leads 130A and 130B, and external programmer 150 shown in conjunction with a patient 105, who is ordinarily a human patient. In the example of FIG. 1, IMD 110 is an implantable electrical stimulator that is configured to generate and deliver electrical stimulation therapy to patient 105 via one or more combinations of electrodes of leads 130A and/or 130B (collectively, "leads 130"), e.g., for relief of chronic pain or other symptoms. In other examples, IMD 110 may be coupled to a single lead carrying multiple electrodes or more than two leads each carrying multiple electrodes.

As described herein, IMD 110 is configured to concurrently deliver two or more stimulation waveforms that differ according to at least one stimulation parameters. In some examples, a first set of stimulation signals, pulses, or waveforms, may be configured to elicit detectable evoked compound action potential (ECAP) signals, e.g., that may indicate a perceptible sensation of paresthesia experienced by the patient. ECAPs are a measure of neural recruitment, because each ECAP signal represents the superposition of electrical potentials generated from a population of axons firing in response to an electrical stimulus (e.g., a stimulation pulse). Changes in a characteristic (e.g., an amplitude of a portion of the signal or area under the curve of the signal) of an ECAP signal occur as a function of how many axons have been activated by the delivered stimulation pulse. For a given set of parameter values that define the stimulation pulse and a given distance between the electrodes and target nerve, the detected ECAP signal may have a certain characteristic value (e.g., amplitude). In some examples, effective stimulation therapy may rely on a certain level of neural recruitment at a target nerve. This effective stimulation therapy may provide relief from one or more conditions (e.g., patient perceived pain) without an unacceptable level of side effects (e.g., overwhelming perception of stimulation). Accordingly, in some scenarios detailed further below, IMD 110 may use detected ECAP signals to determine how to adjust one or more parameters that define stimulation therapy. Additionally or alternatively, a second set of stimulation signals, pulses, or waveforms may be configured to modulate a neurochemical process within the patient, and may not elicit detectable ECAP signals or sensations of paresthesia perceptible to the patient, as detailed further below.

IMD 110 may be a chronic electrical stimulator that remains implanted within patient 105 for weeks, months, or even years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted within other suitable sites within patient 105, which may depend, for example, on the target site within patient 105 for the delivery of electrical stimulation therapy. The outer housing of IMD 110 may be configured to provide a hermetic seal for components, such as for a rechargeable or non-rechargeable power source. In addition, in some examples, the outer housing of IMD 110 is selected from a material that facilitates receiving energy to charge the rechargeable power source.

Electrical stimulation energy, which may be constant-current or constant-voltage-based pulses, for example, is delivered from IMD 110 to one or more target tissue sites of patient 105 via one or more electrodes (not shown) of implantable leads 130. In the example of FIG. 1, leads 130 carry electrodes that are placed adjacent to the target tissue of spinal cord 120. One or more of the electrodes may be disposed at a distal tip of a lead 130 and/or at other positions at intermediate points along the lead. Leads 130 may be implanted and coupled to IMD 110. The electrodes may transfer electrical stimulation generated by an electrical stimulation generator in IMD 110 to tissue of patient 105. Although leads 130 may each be a single lead, lead 130 may include a lead extension or other segments that may aid in implantation or positioning of lead 130. In some other examples, IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration.

The deployment of electrodes via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 130 are linear leads having eight ring electrodes along the axial length of the lead. In another example, the electrodes are segmented rings arranged in a linear fashion along the axial length of the lead and at the periphery of the lead.

The stimulation parameter set of a stimulation program, which defines the stimulation pulses and/or waveform of electrical stimulation therapy by IMD 110 through the electrodes of leads 130, may include information identifying, for example: which electrodes have been selected for delivery of stimulation according to a stimulation program (i.e., the "electrode combination" for the program), the polarities of the selected electrodes, voltage or current amplitude, pulse frequency, pulse width, or pulse shape of electrical stimulation delivered by the electrodes. These stimulation-parameter values, that make up the stimulation-parameter set that defines stimulation pulses, may be predetermined parameter values defined by a user and/or automatically determined by system 100 based on one or more factors or user input. According to techniques of this disclosure, IMD 110 is configured to concurrently deliver two or more distinct periodic waveforms of pulses, such as simultaneously, interleaved, and/or delivered on an intermittent basis. In some examples, IMD 110 may concurrently deliver multiple waveforms via one or more common electrodes of leads 130, e.g., from a common electrode combination or from different electrode combinations that share at least one electrode in common. In other examples, IMD 110 may deliver a different waveform on each of a distinct subset of electrodes of leads 130, e.g., distinct electrode combinations that do not share any common individual electrodes.

Although FIG. 1 is depicted and described with respect to SCS therapy, e.g., used to treat pain, in other examples, system 100 may be configured to treat any other condition that may benefit from electrical stimulation therapy. For example, system. 100 may be used to treat tremor, Parkinson's disease, epilepsy, a pelvic-floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive-compulsive disorder, anxiety disorders, and the like). In this manner, system 100 may be configured to provide therapy taking the form of deep brain stimulation (DBS), peripheral-nerve stimulation (PNS), peripheral-nerve field stimulation (PNFS), cortical stimulation (CS), pelvic-floor stimulation, gastrointestinal stimulation, or any other stimulation therapy capable of treating a condition of patient 105.

In some examples, lead 130 includes one or more sensors configured to enable IMD 110 to monitor one or more parameters of patient 105, such as patient activity, pressure, temperature, or other characteristics. The one or more sensors may be provided in addition to, or in place of, the delivery of therapy via lead 130.

IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle, or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced into spinal cord 120 in via any suitable region, such as the thoracic, cervical, or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which may be reduce the perception of pain by patient 105, and thus, provide efficacious therapy results.

IMD 110 is configured to generate and deliver electrical stimulation therapy to a target stimulation site within patient 105 via the electrodes of leads 130 to patient 105 according to one or more "therapy" stimulation programs (as distinguished from "ECAP" stimulation programs, described below). A therapy stimulation program defines values for one or more parameters (e.g., a parameter set) that define an aspect of the therapy delivered by IMD 110 according to that program. For example, a therapy stimulation program that controls delivery of stimulation by IMD 110 in the form of electrical pulses may define values for amplitudes of voltages or currents, pulse widths, pulse rates (e.g., pulse frequencies), electrode combinations, pulse shapes, etc. for stimulation pulses delivered by IMD 110 according to that program.

Furthermore, IMD 110 may be configured to deliver stimulation to patient 105 via a combination of electrodes of leads 130, alone or in combination with an electrode carried by or defined by an outer housing of IMD 110, in order to detect ECAP signals. The tissue targeted by the stimulation may be the same or similar tissue targeted by the electrical stimulation therapy, but IMD 110 may deliver stimulation pulses for ECAP signal detection via the same, at least some of the same, or different electrodes.

IMD 110 can deliver stimulation to a target stimulation site within patient 105 via the electrodes of leads 130 according to one or more ECAP stimulation programs to develop a growth curve of the ECAP. The one or more ECAP stimulation programs may be stored in a storage device of IMD 110. Each ECAP program of the one or more ECAP stimulation programs includes values for one or more parameters that define an aspect of the stimulation delivered by IMD 110 according to that program, such as current or voltage amplitude, pulse width, pulse frequency, electrode combination. In some examples, the ECAP stimulation program may also define the number of pules and parameter values for each pulse of multiple pulses within a pulse sweep configured to obtain a plurality of ECAP signals for respective pulses in order to obtain the growth curve that IMD 110 may use to determine an estimated neural threshold of the patient. In some examples, IMD 110 delivers stimulation to patient 105 according to multiple ECAP stimulation programs, Although these functions are described with respect to IMD 110, other devices, such as external programmer 150, may perform these functions such as determining a triggering condition and independently modulating two or more concurrent stimulation waveforms.

A user, such as a clinician or patient 105, may interact with a user interface of an external programmer 150 to program IMD 110. Programming of IMD 110 may refer generally to the generation and transfer of commands, programs, or other information to control the operation of IMD 110. In this manner, IMD 110 may receive the transferred commands and programs from external programmer 150 to control stimulation, such as electrical stimulation therapy to develop the growth curve. For example, external programmer 150 may transmit therapy stimulation programs, ECAP stimulation programs, stimulation parameter adjustments, therapy stimulation program selections, ECAP program selections, waveform modulation programs, user input, or other information to control the operation of IMD 110, e.g., by wireless telemetry or wired connection.

In some cases, external programmer 150 may be characterized as a "physician programmer" or "clinician programmer" if it is primarily intended for use by a physician or clinician. In other cases, external programmer 150 may be characterized as a "patient programmer" if it is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change electrical stimulation therapy, when a patient perceives stimulation being delivered or when a patient terminates due to comfort level. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

As described herein, information may be transmitted between external programmer 150 and IMD 110. Therefore, IMD 110 and external programmer 150 may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the IMD 110 implant site to improve the quality or security of communication between IMD 110 and external programmer 150. Communication between external programmer 150 and IMD 110 may occur during power transmission or separate from power transmission.

In some examples, IMD 110, in response to commands from external programmer 150, delivers electrical stimulation therapy according to a plurality of therapy stimulation programs to a target tissue site of the spinal cord 120 of patient 105 via electrodes (not depicted) on leads 130. In some examples, IMD 110 modifies therapy stimulation programs as therapy needs of patient 105 evolve over time. For example, the modification of the therapy stimulation programs may cause the adjustment of at least one parameter of the plurality of therapy pulses. When patient 105 receives the same therapy for an extended period, the efficacy of the therapy may be reduced. In some cases, parameters of the plurality of therapy pulses may be automatically updated. In some examples, IMD 110 may detect ECAP signals from pulses delivered for the purpose of providing therapy to the patient.

In some examples, efficacy of electrical stimulation therapy may be indicated by one or more characteristics of an action potential that is evoked by a stimulation pulse delivered by IMD 110, for example by determining an estimated neural response using the characteristic value of the ECAP signal. Electrical stimulation therapy delivery by leads 130 of IMD 110 may cause neurons within the target tissue to evoke a compound action potential that travels up and down the target tissue, eventually arriving at sensing electrodes of IMD 110. Furthermore, stimulation pulses may also elicit at least one ECAP signal, and ECAPs responsive to stimulation may also be a surrogate for the effectiveness of the therapy and/or the intensity perceived by the patient. The number of action potentials (e.g., number of neurons propagating action potential signals) that are evoked may be based on the various parameters of electrical stimulation pulses such as amplitude, pulse width, frequency, pulse shape (e.g., slew rate at the beginning and/or end of the pulse), etc. The slew rate may define the rate of change of the voltage and/or current amplitude of the pulse at the beginning and/or end of each pulse or each phase within the pulse. For example, a very high slew rate indicates a steep or even near-vertical edge of the pulse, and a low slew rate indicates a longer ramp up (or ramp down) in the amplitude of the pulse. In some examples, these parameters contribute to an intensity of the electrical stimulation. In addition, a characteristic of the ECAP signal (e.g., an amplitude) may change based on the distance between the stimulation electrodes and the nerves subject to the electrical field produced by the delivered control stimulation pulses.

As detailed further below, some example techniques of this disclosure include modulating a stimulation waveform (e.g., adjusting stimulation parameter values for pulses configured to contribute to therapy for the patient) based on comparing the value of a characteristic of a measured ECAP signal to a target ECAP characteristic value. These example waveform-modulation techniques may be referred to as "closed-loop control policies based on ECAP values." In some examples, the target ECAP characteristic value may be the estimated neural threshold or a value calculated based on the estimated neural threshold (e.g., a percentage below or above 100% of the estimated neural threshold). During delivery of control stimulation pulses defined by one or more ECAP test stimulation programs, IMD 110, via two or more electrodes interposed on leads 130, senses electrical potentials of tissue of the spinal cord 120 of patient 105 to measure the electrical activity of the tissue. IMD 110 senses ECAPs from the target tissue of patient 105, e.g., with electrodes on one or more leads 130 and associated sense circuitry. In some examples, IMD 110 receives a signal indicative of the ECAP from one or more sensors, e.g., one or more electrodes and circuitry, internal or external to patient 105. Such an example signal may include a signal indicating an ECAP of the tissue of patient 105.

In the example of FIG. 1, IMD 110 is described as performing a plurality of processing and computing functions. However, external programmer 150 instead may perform one, several, or all of these functions. In this alternative example, IMD 110 functions to relay sensed signals to external programmer 150 for analysis, and external programmer 150 transmits instructions to IMD 110 to adjust the one or more parameters defining the electrical stimulation therapy based on analysis of the sensed signals. For example, IMD 110 may relay the sensed signal indicative of an ECAP to external programmer 150. External programmer 150 may compare the parameter value of the ECAP to the target ECAP characteristic value relative to an estimated neural response, and in response to the comparison, external programmer 150 may instruct IMD 110 to adjust one or more stimulation parameter that defines the electrical stimulation pulses delivered to patient 105.

In the example techniques described in this disclosure, IMD 110 (and/or external programmer 150) is configured to independently modulate each of a plurality of electrical stimulation waveforms, when IMD 110 delivers two or more waveforms to a patient concurrently. As used herein, a stimulation "waveform" may include a "train" of discrete stimulation pulses, a continuous electrical signal of varying amplitude, for example, applied via a single electrode combination, or a combination thereof. More specifically, IMD 110 is configured to determine, identify, or detect a set of "triggering" criteria or conditions objectively defining a predetermined scenario, and then independently modulate at least one of the two or more stimulation waveforms in response to determining the criteria or conditions. In this way, IMD 110 may better maintain patient comfort, improve patient outcomes, improve management of resources, or provide any of a number of other similar practical applications and benefits, as described further herein.

As one illustrative example, IMD 110 may be configured to independently manage two or more concurrent stimulation waveforms, such as by modifying only one of the waveforms according to a waveform modulation program, or by modifying each of the waveforms according to different waveform modulation programs, as illustrated by various non-limiting examples described with respect to FIG. 5, below. In some examples (but not all examples) described herein, the two or more stimulation waveforms may include both a "perceptible" waveform (e.g., electrical stimulation that produces an effect, such as paresthesia, that may be perceived by the patient) and an "imperceptible" waveform, which may not produce patient-perceivable effects. A patient may perceive stimulation when the stimulation intensity exceeds a first perception threshold or sensory threshold. A patient may not perceive stimulation when the stimulation intensity is below a perception threshold or the sensory threshold. In some such examples, IMD 110 may be configured to selectively modulate either or both of the waveforms to maintain or improve therapeutic effects for the patient. Additionally, or alternatively, IMD 110 may be configured to independently modulate either or both waveforms so as to conserve battery capacity, e.g., for an internal battery of IMD 110. Each stimulation waveform may include one or more pulse trains delivered via an electrode combination. Different waveforms and/or different electrode combinations may be associated with different or the same perception or sensory thresholds.

One or more devices within system 100, such as IMD 110 and/or external programmer 150, may perform various functions as described herein. For example, IMD 110 may include stimulation circuitry configured to deliver electrical stimulation, sensing circuitry configured to sense a plurality ECAP signals or other patient parameters, and processing circuitry. The processing circuitry may be configured to control the stimulation circuitry to deliver a plurality of electrical stimulation pulses according to two or more waveforms having different frequencies, pulse widths, and/or amplitude values.

In some examples, IMD 110 may include the stimulation circuitry, the sensing circuitry, and the processing circuitry. However, in other examples, one or more additional devices may be part of the system that performs the functions described herein. For example, IMD 110 may include the stimulation circuitry and the sensing circuitry, but external programmer 150 or other external device may include the processing circuitry that at least determines a triggering condition, and in response, independently modulates a first and/or a second stimulation waveform. IMD 110 may transmit sensor data to external programmer 150, for example. Therefore, the processes described herein may be performed by multiple devices in a distributed system. In some examples, system 100 may include one or more electrodes that deliver and/or sense electrical signals. Such electrodes may be configured to sense ECAP signals. In some examples, the same electrodes may be configured to sense signals representative of transient movements of the patient. In other examples, other sensors, such as accelerometers, gyroscopes, or other movement sensors may be configured to sense movement of the patient that indicates the patient may have transitioned to a different posture state.

In some examples, system 100 (which may be or may include IMD 110 and/or external programmer 150 or off-site or networked computing systems) may include a stimulation generator (or "stimulation generation circuitry") configured to deliver a stimulation pulse to patient 105 and sensing circuitry configured to sense an ECAP signal evoked from the stimulation pulse. System 100 may also include processing circuitry configured to modulate a perceptible stimulation waveform in response to the sensed ECAP signal, according to an ECAP-servoed, closed-loop waveform-modulation program, as detailed further below. The patient or clinician may further modify the stimulation therapy, for example, based on patient preference or expected battery life, for example.

Although in one example IMD 110 takes the form of an SCS device, in other examples, IMD 110 takes the form of any combination of deep brain stimulation (DBS) devices, peripheral-nerve stimulators, pelvic nerve stimulators, implantable cardioverter defibrillators (ICDs), pacemakers, cardiac-resynchronization therapy devices (CR-T-Ds), left-ventricular-assist devices (LVADs), implantable sensors, orthopedic devices, or drug pumps, as examples. Moreover, techniques of this disclosure may be used to determine stimulation thresholds (e.g., perception thresholds and detection thresholds) associated any one of the aforementioned IMDs and then use a stimulation threshold to inform the intensity (e.g., stimulation levels) of therapy.

Figure 2:
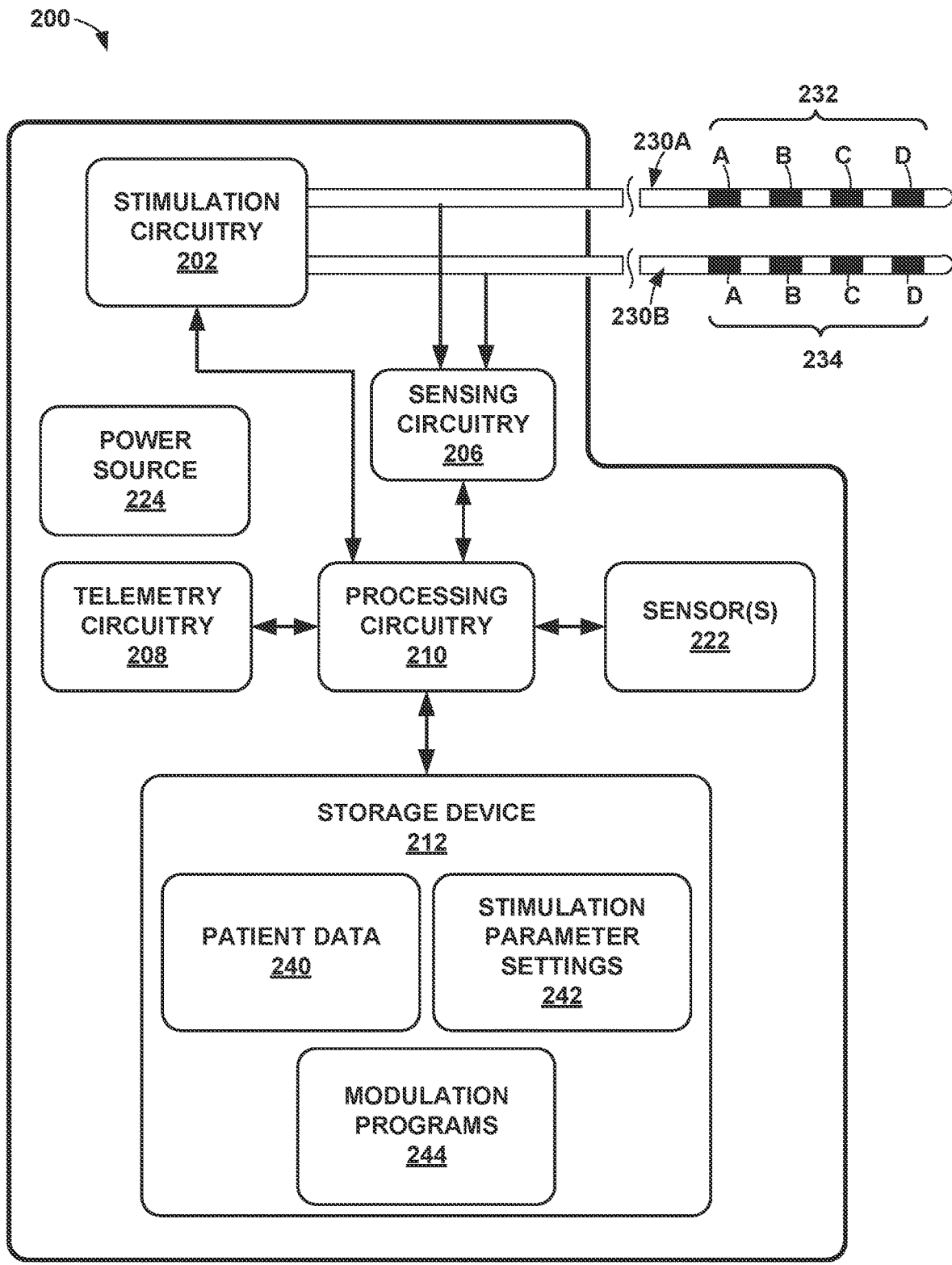
FIG. 2 is a block diagram illustrating an example configuration of components of the IMD of FIG. 1, in accordance with techniques of this disclosure.

FIG. 2 is a block diagram illustrating an example configuration of components of an IMD 200, in accordance with one or more techniques of this disclosure. IMD 200 may be an example of IMD 110 of FIG. 1. In the example shown in FIG. 2, IMD 200 includes stimulation generation circuitry 202, sensing circuitry 206, telemetry circuitry 208, processing circuitry 210, storage device 212, sensor(s) 222, and power source 224.

In the example shown in FIG. 2, storage device 212 stores patient data 240, stimulation parameter settings 242, and ECAP detection instructions 244 in separate memories within storage device 212 or separate areas within storage device 212. Patient data 240 may include parameter values, target characteristic values, or other information specific to the patient. In some examples, stimulation parameter settings 242 may include stimulation parameter values for respective different stimulation programs selectable by the clinician or patient for therapy. In this manner, each stored therapy stimulation program, or set of stimulation parameter values, of stimulation parameter settings 242 defines values for a set of electrical stimulation parameters (e.g., a stimulation parameter set), such as a stimulation electrode combination, electrode polarity, current or voltage amplitude, pulse width, pulse rate, and pulse shape, or duty cycle. Storage device 212 may also store ECAP detection instructions 244 that defines values for a set of electrical stimulation parameters configured to elicit a detectable ECAP signal, such as a stimulation electrode combination, electrode polarity, current or voltage amplitude, pulse width, pulse rate, and pulse shape. ECAP detection instructions 244 may also have additional information such as instructions regarding when to deliver control pulses based on the pulse width and/or frequency of the pulses defined in stimulation parameter settings 242, detection windows for detecting ECAP signals, instructions for determining characteristic values from ECAP signals, etc.

Accordingly, in some examples, stimulation generation circuitry 202 generates electrical stimulation signals in accordance with the electrical stimulation parameters noted above. Other ranges of stimulation parameter values may also be useful and may depend on the target stimulation site within patient 105. While stimulation pulses are described, stimulation signals may be of any form, such as continuous-time signals (e.g., sine waves) or the like.

In this example, stimulation generation circuitry 202 includes a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234. Stimulation generation circuitry 202 and/or sensing circuitry 206 may include switch circuitry to direct signals to and/or from one or more of electrodes 232, 234. In this manner, one or more switches may decouple stimulation circuitry 202 from electrodes 232, 234 and/or sensing circuitry 206 in order to sense signals from the patient via electrodes 232, 234.

In other examples, switch circuitry provides an interface between stimulation generation circuitry 202 and electrodes 232, 234. The switch circuitry may include one or more switch arrays, one or more multiplexers, one or more switches (e.g., a switch matrix or other collection of switches), or other electrical circuitry configured to direct stimulation signals from stimulation generation circuitry 202 to one or more of electrodes 232, 234, or directed sensed signals from one or more of electrodes 232, 234 to sensing circuitry 206.

Sensing circuitry 206 is configured to monitor signals from any combination of electrodes 232, 234. In some examples, sensing circuitry 206 includes one or more amplifiers, filters, and analog-to-digital converters. Sensing circuitry 206 may be used to sense physiological signals, such as ECAP signals. In some examples, sensing circuitry 206 detects ECAPs from a particular combination of electrodes 232, 234. In some cases, the particular combination of electrodes for sensing ECAPs includes different electrodes than a set of electrodes 232, 234 used to deliver stimulation pulses. Alternatively, in other cases, the particular combination of electrodes used for sensing ECAPs includes at least one of the same electrodes as a set of electrodes used to deliver stimulation pulses to patient 105. Sensing circuitry 206 may provide signals to an analog-to-digital converter, for conversion into a digital signal for processing, analysis, storage, or output by processing circuitry 210.

Telemetry circuitry 208 supports wireless communication between IMD 200 and an external programmer (not shown in FIG. 2) or another computing device under the control of processing circuitry 210, Processing circuitry 210 of IMD 200 may receive, as updates to programs, values for various stimulation parameters such as amplitude and electrode combination, from the external programmer via telemetry circuitry 208. Processing circuitry 210 may store updates to the stimulation parameter settings 242 or any other data in storage device 212. Telemetry circuitry 208 in IMD 200, as well as telemetry circuits in other devices and systems described herein, such as the external programmer, may accomplish communication by radiofrequency (RF) communication techniques. In addition, telemetry circuitry 208 may communicate with an external medical device programmer (not shown in FIG. 2) via proximal inductive interaction of IMD 200 with the external programmer. The external programmer may be one example of external programmer 150 of FIG. 1. Accordingly, telemetry circuitry 208 may send information to the external programmer on a continuous basis, at periodic intervals, or upon request from IMD 110 or the external programmer.

Processing circuitry 210 may include any one or more of a microprocessor, a controller, a digital signal processor (DSP), an application-specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 controls stimulation generation circuitry 202 to generate stimulation signals according to stimulation parameter settings 242 and any other instructions stored in storage device 212 to apply stimulation parameter values specified by one or more of programs, such as amplitude, pulse width, pulse rate, and pulse shape of each of the stimulation signals.

In the example shown in FIG. 2, the set of electrodes 232 includes electrodes 232A, 232B, 232C, and 232D, and the set of electrodes 234 includes electrodes 234A, 234B, 234C, and 234D. In other examples, a single lead may include all eight electrodes 232 and 234 along a single axial length of the lead. Processing circuitry 210 also controls stimulation generation circuitry 202 to generate and apply the stimulation signals to selected combinations of electrodes 232, 234. In some examples, stimulation generation circuitry 202 includes a switch circuit that may couple stimulation signals to selected conductors within leads 230, which, in turn, deliver the stimulation signals across selected electrodes 232, 234. Such a switch circuit may be a switch array, switch matrix, multiplexer, or any other type of switching circuit configured to selectively couple stimulation energy to selected electrodes 232, 234 and to selectively sense bioelectrical neural signals of a spinal cord of the patient (not shown in FIG. 2) with selected electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generation circuitry 202, e.g., via independent switch circuitry and/or switching circuitry of the stimulation generation circuitry 202, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 206 is incorporated into a common housing with stimulation generation circuitry 202 and processing circuitry 210 in FIG. 2, in other examples, sensing circuitry 206 may be in a separate housing from IMD 200 and may communicate with processing circuitry 210 via wired or wireless communication techniques. In some examples, one or more of electrodes 232 and 234 are suitable for sensing the ECAPs. For instance, electrodes 232 and 234 may sense the voltage amplitude of a portion of the ECAP signals, where the sensed voltage amplitude, such as the voltage difference between features within the signal, is a characteristic the ECAP signal.

Storage device 212 may be configured to store information within IMD 200 during operation. Storage device 212 may include a computer-readable storage medium or computer-readable storage device. In some examples, storage device 212 includes one or more of a short-term memory or a long-term memory. Storage device 212 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM), In some examples, storage device 212 is used to store data indicative of instructions for execution by processing circuitry 210. As discussed above, storage device 212 is configured to store patient data 240, stimulation parameter settings 242, and waveform-modulation programs 244.

Sensor(s) 222 may include one or more sensing elements that sense values of a respective patient parameter, such as posture state. As described, electrodes 232 and 234 may be the electrodes that sense the characteristic value of the ECAP signal. Sensor(s) 222 may include one or more accelerometers, optical sensors, chemical sensors, temperature sensors, pressure sensors, or any other types of sensors. Sensor(s) 222 may output patient parameter values that may be used as feedback to control delivery of therapy. For example, sensor(s) 222 may indicate patient activity, and processing circuitry 210 may implement a waveform-modulation program (e.g., increase the frequency of control pulses and/or ECAP sensing) in response to detecting increased patient activity. In one example, processing circuitry 210 may initiate control pulses and corresponding ECAP sensing in response to a signal from sensor(s) 222 indicating that patient activity has exceeded an activity threshold. Conversely, processing circuitry 210 may decrease the frequency of control pulses and ECAP sensing in response to detecting decreased patient activity. For example, in response to sensor(s) 222 no longer indicating that the sensed patient activity exceeds a threshold, processing circuitry 210 may suspend or stop delivery of control pulses and ECAP sensing. In this manner, processing circuitry 210 may dynamically deliver control pulses and sense ECAP signals based on patient activity to reduce power consumption of the system when the electrode-to-neuron distance is not likely to change and increase system response to ECAP changes when electrode-to-neuron distance is likely to change.

IMD 200 may include additional sensors within the housing of IMD 200 and/or coupled via one of leads 130 or other leads. In addition, IMD 200 may receive sensor signals wirelessly from remote sensors via telemetry circuitry 208, for example. In some examples, one or more of these remote sensors may be external to patient 105 (e.g., carried on the external surface of the skin, attached to clothing, or otherwise positioned external to patient 105). In some examples, signals from sensor(s) 222 indicate a position or body state (e.g., sleeping, awake, sitting, standing, or the like), and processing circuitry 210 may select a corresponding waveform-modulation program, e.g., including target ECAP characteristic values, according to the indicated position or body state.

Power source 224 is configured to deliver operating power to the components of IMD 200. Power source 224 may include a battery and a power generation circuit to produce the operating power. In some examples, the battery is rechargeable to allow extended operation. In some examples, recharging is accomplished through proximal inductive interaction between an external charger and an inductive charging coil within IMD 200. Power source 224 may include any one or more of a plurality of different battery types, such as nickel cadmium batteries and lithium ion batteries.

In some examples, storage device 212 may store waveform-modulation programs 244. Modulation programs 244 may include, for example, articulable criteria for modulating one or more parameters of a stimulation waveform in response to a detected triggering condition or determined scenario. As detailed further below with respect to FIG. 5, modulation programs 244 can instruct processing circuitry 210 how to cause stimulation circuitry 202 to modify the delivery of electrical stimulation in a scenario defined by objective criteria, which may be programmed by the patient, the clinician, or according to default programming. Waveform-modulation programs 244 include specific techniques for modifying stimulation parameters such as pulse width, pulse amplitude, pulse frequency, etc., in response to determining triggering conditions. As used herein, a "triggering condition" may include any of a number of predetermined or predefined threshold values, or a combination thereof, that indicate the presence of a situation, scenario, or conditions that presently or imminently have an effect on the stimulation therapy in some form. In some cases, the triggering condition may indicate the presence of a constraint on the therapy system. Some non-limiting examples of triggering conditions include the receipt of a particular value of sensor data, user input, a detected low battery capacity of power source 224 of IMD 200, or the like, that exceeds a threshold value. Further examples of triggering conditions and corresponding waveform-modulation programs are detailed below.

Figure 3:
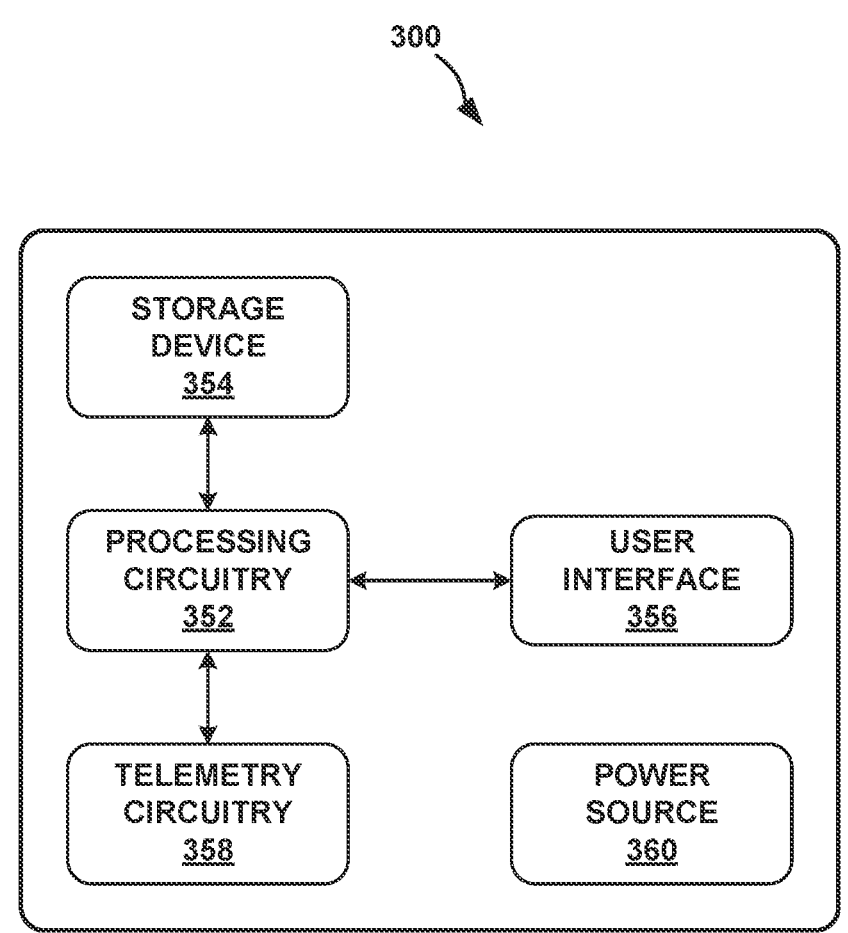
FIG. 3 is a block diagram illustrating an example configuration of components of the external programmer of FIG. 1, in accordance with techniques of this disclosure.

FIG. 3 is a block diagram illustrating an example configuration of components of an example external programmer 300. External programmer 300 may be an example of external programmer 150 of FIG. 1. Although external programmer 300 may generally be described as a hand-held device, external programmer 300 may be a larger portable device or a more stationary device. In addition, in other examples, external programmer 300 may be included as part of an external charging device or include the functionality of an external charging device. As illustrated in FIG. 3, external programmer 300 may include processing circuitry 352, storage device 354, user interface 356, telemetry circuitry 358, and power source 360. Storage device 354 may store instructions that, when executed by processing circuitry 352, cause processing circuitry 352 and external programmer 300 to provide the functionality ascribed to external programmer 300 throughout this disclosure. Each of these components, circuitry, or modules, may include electrical circuitry that is configured to perform, some, or all of the functionality described herein. For example, processing circuitry 352 may include processing circuitry configured to perform the processes discussed with respect to processing circuitry 352.

In general, external programmer 300 includes any suitable arrangement of hardware, alone or in combination with software and/or firmware, to perform the techniques attributed to external programmer 300, and processing circuitry 352, user interface 356, and telemetry circuitry 358 of external programmer 300. In various examples, external programmer 300 may include one or more processors, such as one or more microprocessors, DSPs, ASICs, FPGAs, or any other equivalent integrated or discrete logic circuitry, as well as any combinations of such components. External programmer 300 also, in various examples, may include a storage device 354, such as R-M/I, ROM, PROM, EPROM, EEPROM, flash memory, a hard disk, a CD-ROM, including executable instructions for causing the one or more processors to perform the actions attributed to them. Moreover, although processing circuitry 352 and telemetry circuitry 358 are described as separate modules, in some examples, processing circuitry 352 and telemetry circuitry 358 are functionally integrated. In some examples, processing circuitry 352 and telemetry circuitry 358 correspond to individual hardware units, such as ASICs, DSPs, FPGAs, or other hardware units.

Storage device 354 (e.g., a storage device) may store instructions that, when executed by processing circuitry 352, cause processing circuitry 352 and external programmer 300 to provide the functionality ascribed to external programmer 300 throughout this disclosure. For example, storage device 354 may include instructions that cause processing circuitry 352 to independently modulate two or more stimulation waveforms, or instructions for any other functionality. In addition, storage device 354 may include a plurality of programs, where each program includes a parameter set that defines therapy stimulation or control stimulation. Storage device 354 may also store data received from a medical device (e.g., IMD 110). For example, storage device 354 may store ECAP related data recorded at a sensing module of the medical device, and storage device 354 may also store data from one or more sensors of the medical device.

User interface 356 may include a button or keypad, lights, a speaker for voice commands, a display, such as a liquid crystal display (LCD), light-emitting diode (LED), or organic light-emitting diode (OLED). In some examples the display includes a touch screen. User interface 356 may be configured to display any information related to the delivery of electrical stimulation, identified posture states, sensed patient parameter values, or any other such information. User interface 356 may also receive user input (e.g., indication of when the patient perceives a stimulation pulse) via user interface 356. The input may be, for example, in the form of pressing a button on a keypad or selecting an icon from a touch screen. The input may request starting or stopping electrical stimulation, the input may request a new spatial electrode pattern or a change to an existing spatial electrode pattern, of the input may request some other change to the delivery of electrical stimulation.

Telemetry circuitry 358 may support wireless communication between the medical device and external programmer 300 under the control of processing circuitry 352. Telemetry circuitry 358 may also be configured to communicate with another computing device via wireless communication techniques, or direct communication through a wired connection. In some examples, telemetry circuitry 358 provides wireless communication via an RF or proximal inductive medium. In some examples, telemetry circuitry 358 includes an antenna, which may take on a variety of forms, such as an internal or external antenna.

Examples of local wireless communication techniques that may be employed to facilitate communication between external programmer 300 and IMD 110 include RF communication according to the 802.11 or Bluetooth® specification sets or other standard or proprietary telemetry protocols. In this manner, other external devices may be capable of communicating with external programmer 300 without needing to establish a secure wireless connection. Telemetry circuitry 358 may be configured to transmit a spatial electrode movement pattern or other stimulation parameter values to IMD 110 for delivery of electrical stimulation therapy. Although IMD 110 may determine characteristic values for ECAP signals and control the adjustment of stimulation parameter values in some examples, programmer 300 may perform these tasks alone or together with IMD 110 in a distributed function.

In some examples, selection of stimulation parameters or therapy stimulation programs are transmitted to the medical device for delivery to a patient (e.g., patient 105 of FIG. 1). In other examples, the therapy may include medication, activities, or other instructions that patient 105 must perform themselves or a caregiver perform for patient 105. In some examples, external programmer 300 provides visual, audible, and/or tactile notifications that indicate there are new instructions. External programmer 300 requires receiving user input acknowledging that the instructions have been completed in some examples.

User interface 356 of external programmer 300 may also be configured to receive an indication from a clinician instructing a processor of the medical device to update one or more therapy stimulation programs or to implement a particular modulation program. Updating therapy stimulation programs and target characteristic values may include changing one or more parameters of the stimulation pulses delivered by the medical device according to the programs, such as amplitude, pulse width, frequency, and pulse shape of the pulses and/or control pulses. User interface 356 may also receive instructions from the clinician commanding any electrical stimulation, including therapy stimulation and control stimulation to commence or to cease.

Power source 360 is configured to deliver operating power to the components of external programmer 300. Power source 360 may include a battery and a power generation circuit to produce the operating power. In some examples, the battery is rechargeable to allow extended operation. Recharging may be accomplished by electrically coupling power source 360 to a cradle or plug that is connected to an alternating current (AC) outlet. In addition, recharging may be accomplished through proximal inductive interaction between an external charger and an inductive charging coil within external programmer 300. In other examples, traditional batteries (e.g., nickel cadmium or lithium ion batteries) may be used. In addition, external programmer 300 may be directly coupled to an AC outlet to operate.

The architecture of external programmer 300 illustrated in FIG. 3 is shown as an example. The techniques as set forth in this disclosure may be implemented in the example external programmer 300 of FIG. 3, as well as other types of systems not described specifically herein. Nothing in this disclosure should be construed so as to limit the techniques of this disclosure to the example architecture illustrated by FIG. 3.

Figure 4:
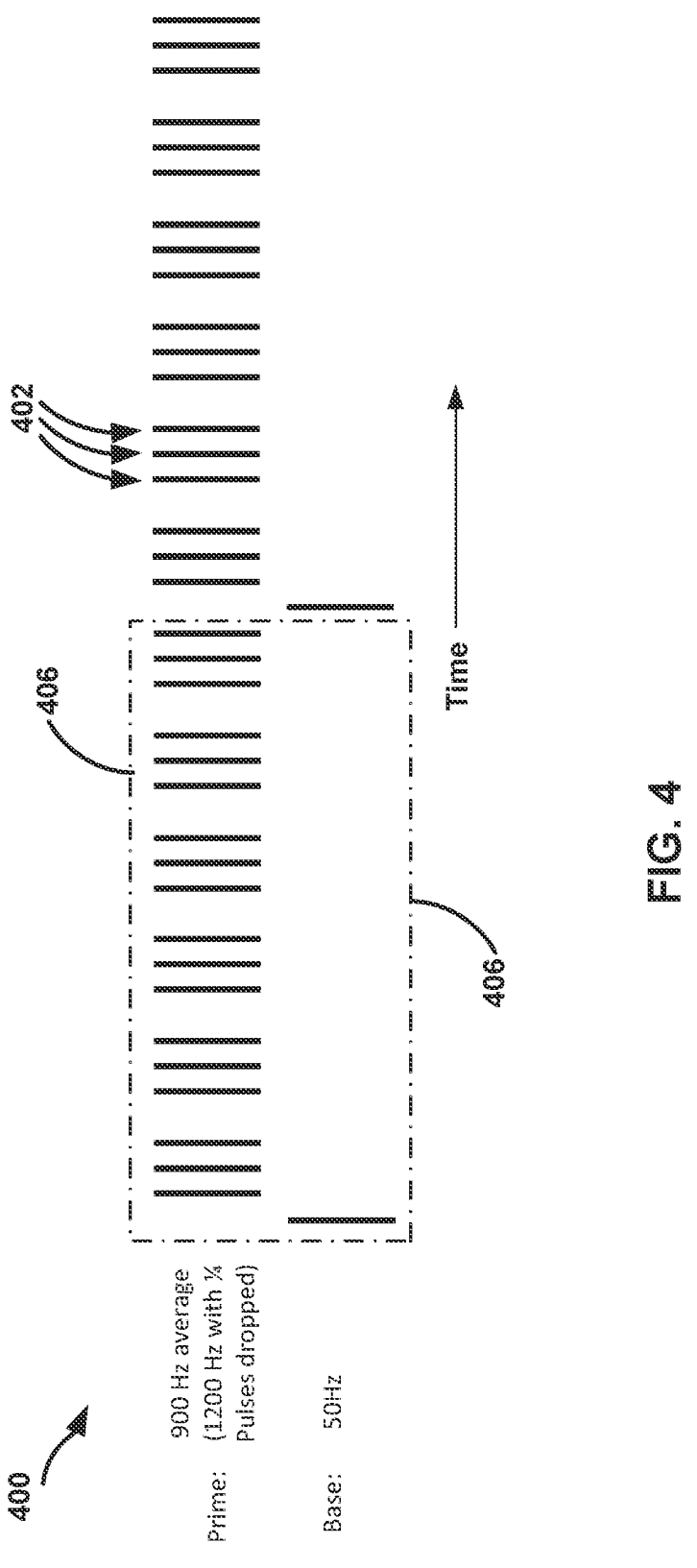
FIG. 4 is a timing diagram illustrating an example of electrical stimulation pulses delivered according to different stimulation patterns.

FIG. 4 is a timing diagram illustrating an example of electrical stimulation pulses delivered according to different stimulation patterns having different pulse frequencies. In one or more examples, the different amplitudes for the stimulation pulses delivered via different electrode combinations (e.g., different tissue locations) may be determined based on an estimated neural threshold. As shown in timing diagram 400, pattern cycle 406 includes repeated groups of pulses over time. The top "prime" pulses can be delivered via one electrode combination and the bottom "base" pulses are delivered to a second electrode combination Each of the pattern cycles are possible with a group rate of 300 Hz (e.g., system rate) for series of slots that includes 4 slots within which pulses 402 can be delivered. In pattern 406, each series of slots has four slots where the first slot includes a pulses for the base stimulation to achieve 50 Hz stimulation, the second, third, and fourth slot includes pulses for respective 300 Hz pulse trains for the prime stimulation. Therefore, the resulting prime stimulation is delivered with an average of 900 Hz frequency over time and an interpulse frequency of 1,200 Hz for three consecutive pulses. Although a group rate of 300 Hz is described, the group rate may be adjusted according to the number of slots in the series of slots and the desired frequencies to achieve for each type of stimulation. In other examples, the base stimulation may have a frequency of approximately 60 Hz, 120 Hz, 200 Hz, or any other frequency as needed. For any of the examples of herein, IMD 200 may switch the prime stimulation from one target tissue to another target tissue in order to achieve efficacious therapy.

In some examples, IMD 200 may change the order of pulses of one train of electrical stimulation pulses in the prime train with pulses of another train of electrical stimulation pulses over time to adjust a pulse pattern created by interleaving the at least of the electrical stimulation pulses of the trains of electrical stimulation pulses used to generate the overall prime train of stimulation pulses.

In some examples, the average frequency of the prime stimulation is selected from a frequency range from approximately 100 Hz to approximately 1,200 Hz. In another example, the average frequency of the prime stimulation is selected from a frequency range from approximately 150 Hz to approximately 900 Hz. In another example, the average frequency of the prime stimulation is approximately 200 Hz. The frequency of the base stimulation may be selected from a frequency range from approximately 40 Hz to approximately 60 Hz. In some examples, IMD 200 may include the amplitude of base stimulation until the patient achieves effective pain relief. Pulse frequencies below and/or above these frequency ranges may be used in other examples. Although the prime and base stimulation pulse trains are shown with the prime stimulation having a higher pulse frequency, the prime and base stimulation pulse trains may have the same frequencies or the base stimulation may have a pulse frequency higher than the prime frequency in other examples.

In some examples, IMD 200 may cycle between a first mode of a first period of time and a second mode of a second period of time, wherein the first mode comprises generating the first train of electrical stimulation pulses (e.g., the prime stimulation) at least partially interleaved with the second train of electrical stimulation pulses (e.g., the base stimulation). The second mode may include withholding generation of the first train of electrical stimulation pulses and the second train of electrical stimulation pulses. In some examples, the ratio of the first period to the second period of time is between approximately 1:1 and 1:3. In other examples, the ratio may be lower to enable much longer off periods for stimulation. In one example, the first period of time for stimulation is selected from a range from approximately 1 minute to approximately 30 minutes. In another example, the first period of time for stimulation is selected from a range from approximately 5 minute to approximately 15 minutes. In some examples, the on period for stimulation may be less than 1 minute or greater than 30 minutes.

In some examples, the amplitude of pulses of the first train of electrical stimulation pulses (e.g., the prime stimulation) is below at least one of a perception threshold or a sensory threshold of a patient (e.g., below the estimated neural threshold or a measured threshold). In some examples, the amplitude of pulses of the second train of electrical stimulation pulses (e.g., the base stimulation) is below at least one of a perception threshold or a sensory threshold of a patient (e.g., below the estimated neural threshold). In some examples, the prime stimulation is set at an amplitude value 60% of an estimated neural threshold of a patient. In some examples, the amplitude of pulses for the base stimulation is set at 65% of the estimated neural threshold of a patient. In this manner, the system may automatically determine the estimated neural threshold and, from the estimated neural threshold, the initial stimulation amplitude for the prime and base stimulation pulses. The percentages of the estimated neural threshold here are merely one example. The percentage may be higher or lower than these percentages in other examples.

The amplitude of a priming component may be set at a value below a Priming Perception Threshold (PPT), although setting it at or above the PPT is not excluded. The PPT may be found by slowly increasing the amplitude while feedback is obtained from the subject. Once the onset of perception is recorded, then the amplitude of the priming component may be changed to a value which is a percentage of the PPT (% PPT). Alternatively, the system may use the automatically determined estimated neural threshold instead of the PPT (or as the PPT). With an exemplary pulse frequency (PF) of 200 Hz, the signal may be then set for a given time, e.g., 10-30 minutes, before an electric component set at a tonic frequency lower than the PF, e.g., 10 Hz to 199 kHz, is applied independently to other electrodes in the lead. In the prime mode of stimulation, the tonic frequency will be lower than the priming frequency, but is not necessarily limited to a particular range of frequencies below the priming frequency.

In some examples, stimulation-generation circuitry may generate a first train of electrical stimulation pulses at a first frequency to a first target tissue, and may generate a second train of electrical stimulation pulses at a second frequency to a second target tissue different from the first target tissue. In some examples, at least some electrical stimulation pulses of the first train of electrical stimulation pulses may be interleaved with at least some electrical stimulation pulses of the second train of electrical stimulation pulses, and/or the first frequency may be greater than the second frequency. In one or more examples, processing circuitry may determine amplitude values for the first and second trains of electrical stimulation pulses as respective percentages of the estimated neural threshold. These first and second trains may correspond to the prime stimulation and base stimulation, respectively.

Figure 5:
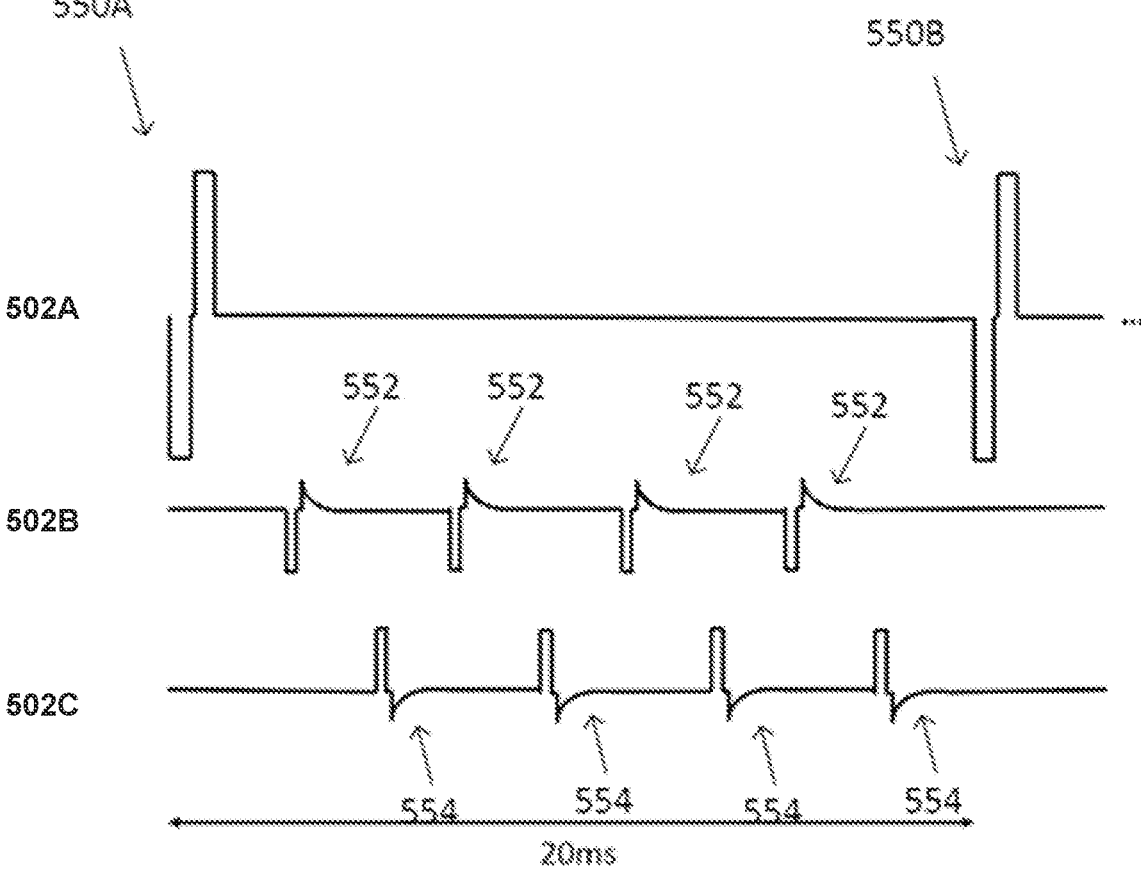
FIG. 5 is a graph illustrating an example of electrical stimulation pulses delivered according to different stimulation waveforms.

FIG. 5 is a graph illustrating another example of electrical stimulation pulses delivered according to different stimulation waveform patterns. As described above with respect to FIG. 1, spinal cord stimulation (SCS) system 100 (including, e.g., IMD 110 of FIG. 1 and/or IMD 200 of FIG. 2) may use the concurrent delivery of multiple different stimulation waveforms to improve or optimize therapeutic outcomes for patient 105. As one non-limiting example of multiple concurrent waveforms, IMD 200 may deliver a first waveform (also referred to as a "stimulation train" or "pulse train") of stimulation pulses having a pulse frequency of about 50 Hz and a pulse width of about 200 μs, e.g., via a first pair of electrodes of leads 230 (FIG. 2). Concurrently, IMD 200 may deliver a second waveform of stimulation pulses having a pulse frequency of about 1000 Hz and a pulse width of about 150 μs another set of electrodes of leads 230. In this example, the first (50 Hz) waveform may be configured to elicit sensations of paresthesia experienced by patient 105, while the second (1000 Hz) waveform may be configured to modulate a neurochemical process of patient 105, and is not configured to be perceived by patient 105. However, these frequencies and pulse widths are merely examples, and stimulation with higher or lower frequencies and/or higher or lower pulse widths may be employed in other examples. For example, the first waveform may have a pulse width from about 120 μs to about 500 μs and a frequency from about 40 Hz to about 50 Hz, and the second waveform may have a pulse width from about 80 μs to about 500 μs and a frequency from about 100 Hz to about 1200 Hz.

In other examples, such as the example depicted in FIG. 5, IMD 200 may be configured to concurrently deliver more than two waveforms 502A-502C. In general, the techniques of this disclosure are described primarily with respect to systems involving two or more distinct waveforms (e.g., that differ in stimulating-electrode location, pulse width, pulse frequency, pulse amplitude, waveshape, or interphase interval). In some of the examples, but not all of the examples described herein, at least one of the waveforms is configured to be at least partly perceptible by patient 105, such as via sensations of paresthesia experienced by patient 105.

In accordance with techniques of this disclosure, in some instances, it is desirable to modulate the two or more waveforms 502A-502C independently from one another. For instance, certain conditions or scenarios may occur that either present a constraint on the stimulation system, or may otherwise have an effect on the stimulation system. There are virtually limitless scenarios that could occur that have such effects or present such constraints, however, a few non-limiting examples of such scenarios or constraints may include: a low remaining battery capacity of IMD 200 that could reduce or abrogate the stimulation therapy; a movement, activity, or change in position of patient 105 that could alter the effect of the stimulation therapy on patient 105, e.g., due to movement of the electrodes relative to the tissue of patient 105; a change in symptoms, neurochemical process, or other dynamic biological parameter occurring within patient 105; and a change in any conditions of an environment in which patient 105 is located.

In any such scenario, or any other scenario of this nature in which a change in IMD 200, patient 105, or local environmental conditions presents a potential effect on stimulation therapy, selective, independent modulation of any or all of the stimulation waveforms may provide a number of practical applications and benefits, such as, but not limited to: maintaining or improving therapeutic outcomes for patient 105, controlling a neurochemical process that is not well-suited to either continuous or interrupted electrical stimulation therapy or to dependent (e.g., correlated) modulation of all the waveforms, and/or conserving resources (e.g., prolonging a battery life of IMD 200).

As described herein, "independent modulation" can refer to any of the techniques of: modulating first electrical stimulation (e.g., a first waveform) without modulating second electrical stimulation (e.g., a second, concurrent waveform); modulating a second waveform without modulating a first concurrent waveform; or modulating a first waveform, according to a first modulation program, and modulating a second waveform according to a second modulation program, wherein the first and second modulation programs are different in at least one respect. For instance, the waveform-modulation program may define a technique for changing any or all of the combination or subset of electrodes is used for electrical stimulation, pulse width, pulse frequency, pulse amplitude, waveshape, interphase interval, or, as explained further below, the type of "looping" mechanism (e.g., closed-loop or open-loop) driving the stimulation therapy according to the stimulation program. Accordingly, the techniques of this disclosure include at least determining the presence of a triggering condition, wherein the triggering condition is indicative of a previously anticipated scenario, condition, constraint, or other actual or potential effect on the stimulation therapy), and in response, independently modulating each of two or more stimulation waveforms in a particular, predetermined manner that addresses the new condition, constraint, etc.

As described above with respect to FIG. 3, the triggering condition may be or may include any or all of a signal received by IMD 200, such as a sensor signal, indicator signal, a user input signal, or the like; a certain threshold data value calculated by ENID 200, such as a threshold battery level of IMD 200; or any combination thereof. Similar to the potential scenarios or conditions described above, the potential triggering conditions that are indicative of such scenarios or conditions are likewise virtually limitless. Accordingly, certain triggering conditions may fit in accordance with the techniques of this disclosure without being explicitly recited herein.

In some examples, IMD 200 may determine, detect, or identify the triggering condition by comparing a received signal or determined value to a set of predetermined triggering-condition signals or values, such as stored in memory 212 of IMD 200. In response to positively identifying one or more triggering conditions, IMD 200 is configured to retrieve a respective therapy-modulation program 244 that is likewise stored in memory 200 and that is associated with the stored triggering condition. The set of therapy-modulation programs 244 may be pre-programmed into memory 212, e.g., by a clinician of patient 150, by patient 150 according to patient preferences, at the time of manufacture, or via automatic updates (e.g., for therapy-modulation programs having general applicability to all patients under a common set of scenarios or conditions). The retrieved therapy-modulation program 244 is configured to address, utilize, or prevent the scenario or condition indicated by the indicated triggering condition.

As with the potential scenarios and respective triggering conditions, the potential therapy-modulation programs configured to address the potential scenarios are virtually limitless. Accordingly, the following six examples demonstrate some specific applications of the independent waveform-modulation techniques of this disclosure for purposes of illustration of the concept, however, the examples are not intended to be limiting. Other examples of stimulation-therapy-effecting scenarios, respective triggering conditions, and responsive independent-waveform-modulation programs not enumerated herein may nevertheless constitute techniques in accordance with this disclosure.

In one illustrative example of the independent-waveform-modulation techniques of this disclosure, IMD 200 concurrently delivers first stimulation therapy having a first waveform, and second stimulation therapy having a second waveform. The first stimulation waveform includes a pulse frequency of about 50 Hz, and is at least partially perceptible by patient 150, e.g., via induced sensations of paresthesia. In one example, the first stimulation waveform may be selected from a range of 40 Hz to 200 Hz. The second stimulation waveform includes a pulse frequency of about 10 kHz, and is not perceptible by patient 150. In some examples, the second waveform may include a pulse frequency selected from a range of about 200 Hz to 10 kHz, or from about 1000 Hz to about 10 kHz, or from about 200 Hz to about 1200 Hz.

As IMD 200 concurrently delivers the first and second stimulation therapies to patient 150, the stored energy of power source 224 (e.g., an internal battery) of IMD 200 gradually depletes. IM) 200 (e.g., via processing circuitry 210), is configured to monitor the remaining power level of power source 224. At some point, the remaining power level of power source 224 crosses a threshold level, which IMD 200 detects as a triggering condition, e.g., by comparing the present (e.g., currently calculated) power level of power source 224 to an indication of the predetermined "threshold" power level stored in memory 212.

In response to determining the triggering condition of the threshold battery level, IMD 200 retrieves a corresponding therapy modulation program 244 stored in memory 212. For instance, the therapy modulation program 244 may provide instructions for independently modifying one or both of the first and second waveforms, e.g., to conserve battery power while maintaining effective stimulation therapy to the extent possible.

In this first illustrative example, because the first stimulation therapy produces paresthesia perceivable by patient 150, it may be undesirable to fully terminate the first stimulation therapy to conserve battery power, as the sudden cessation of the paresthesia sensation would be noticed by patient 150 and would likely be disruptive to the benefits of the patient's therapy. Accordingly, the retrieved therapy-modulation program 244 includes instructions to modify the second (e.g., imperceptible) stimulation waveform instead, without modifying the first stimulation waveform, in order to conserve battery power. For instance, the retrieved therapy-modulation program 244 may include instructions for IMD 110 to maintain the first waveform of the first stimulation therapy, while modulating a current amplitude and/or voltage amplitude of the second waveform of the second stimulation therapy. In some examples, the retrieved therapy-modulation program 244 may cause IMD 110 to "cycle" the second waveform on-and-off, e.g., in one-minute increments (or in any other suitable time increment selected in the range from about 5 seconds to about 10 minutes, for example). In other examples, the on or off times for cycling may be less than 5 seconds, or greater than 10 minutes for one or both of the on and off periods of the cycle. These cycling periods may be selected and/or adjusted for the specific patient in order to achieve effective therapy. In other examples, the retrieved therapy-modulation program 244 may cause IMD 110 to modulate the current or voltage amplitude of the second waveform to periodically vary between higher and lower amplitudes, without reaching a "zero" amplitude (e.g., without the second electrical stimulation cycling off), in order to conserve battery power. As one illustrative, non-limiting example of this amplitude cycling, IMD 110 may cycle the amplitude of the second waveform from about 1 mA to about 0.5 mA, e.g., in one-minute increments.

In other instances of the first illustrative example of this disclosure, rather than the triggering condition comprising a low-battery indication, the triggering condition may include a determination (e.g., by IMD 200 and/or external programmer 300) of an indication that a fixed, continuous delivery of the second stimulation therapy is no longer necessary for providing successful therapeutic outcomes for the patient. This indication may be, in one example, a period of time of effective therapy where the system automatically begins to start cycling the stimulation with a short off-time, but gradually increases the off-time over a period of days or weeks until the therapy is no longer effective. The system can then return to the previously effective cycling periods. In some other examples of the first illustrative example of this disclosure, the triggering condition may include a determination, e.g., by IMD 200 and/or external programmer 300, of an indication that an indicated neurochemical process of patient 150 is not particularly well-treated by either continuous electrical stimulation or by interrupted electrical stimulation. In such examples, IMD 200 may retrieve a corresponding therapy-modulation program 244 that instructs IMD 200 to modulate the first waveform, the second waveform, or both in order to improve treatment of the indicated neurochemical process for patient 150.

In a second illustrative example of the independent-waveform-modulation techniques of this disclosure, IMD 200 concurrently delivers first and second stimulation therapies, having corresponding waveforms similar to those in the first illustrative example (e.g., a first "perceptible" waveform a second "imperceptible" waveform). In this example, IMD 200 may determine a triggering condition that includes or indicates the presence or absence of an electrophysiologic, positional, biochemical, or time-based marker (or other similar indicator). For instance, IMD 200 may receive sensor data from sensor 222, such as an accelerometer, indicating a relative position, pose, orientation, or movement of patient 150. In response to determining a particular value of the received sensor data, IMD 200 may retrieve and implement a corresponding "first" waveform-modulation program 244 that instructs IMD 200 to modify the current and/or voltage amplitude of the second (e.g., imperceptible) waveform. For example, in scenarios in which the received sensor data indicates that patient 150 is in a reclined or supine position, the retrieved therapy-modulation program 244 may instruct IMD 200 to reduce an amplitude of the second waveform, or even temporarily disable the second waveform. When a patient is in this position, the second waveform may be effective with a lower amplitude or may not be required at all in order to still achieve effective therapy with the first waveform. This reduction in amplitude may be perceived as more effective at reducing symptoms and may also reduce battery consumption by IMD 200.

At a future point in time, IMD 200 may determine a subsequent triggering condition, such as by receiving subsequent sensor data, from sensor 222, indicating that patient 150 is now oriented in an upright position or is in motion. In response, the "first" waveform-modulation program 244 may cause IMD 200 to resume the previous levels of stimulation therapy, e.g., to reenable the second waveform or increase the amplitude of the second waveform, as appropriate.

In some examples (but not in all examples) of the second illustrative example of this disclosure, IMD 200 may additionally or alternatively be configured to retrieve and implement, in response to determining the triggering condition based on the received sensor data, a "second" waveform-modulation program 244 that is different from the first waveform-modulation program 244. For instance, the "second" waveform-modulation program 244 may instruct IMD 200 to modify the first (e.g., perceptible) waveform in a way that is different from the way in which the "first" waveform-modulation program 244 instructs IMD 200 to modify the second (e.g., imperceptible) waveform. For instance, the movement or activity of patient 150 indicated by the sensor data received by sensor (e.g., accelerometer) 222, may also cause corresponding movement of electrode leads 230 relative to the target tissue of patient 150. This motion of electrode leads 230 relative to the patient's tissue may cause undesirable fluctuations in the sensation of paresthesia caused by the first "perceptible" waveform, as experienced by patient 150. Accordingly, while the "first" waveform-modulation program 244 causes IMD 200 to simply reduce or disable the second (imperceptible) stimulation therapy, the "second" waveform-modulation program 244 may cause IMD 200 to dynamically modify the first (perceptible) waveform according to a closed-loop control policy based on detected ECAP values, as described above with respect to FIG. 1. For instance, the "second" waveform-modulation program 244 may cause IMD 200 to begin discretely controlling the current and/or voltage amplitude of the first stimulation waveform on a pulse-to-pulse basis based on received sensor data (e.g., via electrodes 232) indicating detected ECAPs of patient 150. This closed-loop control policy causes IM) 200 to automatically compensate for fluctuations in paresthesia caused by the patient's movement, thereby providing for a more-consistent and pleasant therapy experience for patient 150.

In a third illustrative example of the independent-waveform-modulation techniques of this disclosure, IMD 200 concurrently delivers first and second stimulation therapies, having corresponding waveforms similar to those in the first illustrative example (e.g., a first "perceptible" waveform a second "imperceptible" waveform). At some point, IMD 200 determines a triggering condition, such as the patient-position or patient-movement indicated by received accelerometer data, as described in the second illustrative example above. In response to determining the triggering condition, IMD 200 retrieves a waveform-modulation program 244 that instructs IMD 200 to modulate the first (perceptible) waveform without modulating the second (imperceptible)

waveform. For instance, the retrieved waveform-modulation program 244 may instruct IMD 200 to modulate the first (perceptible) waveform according to the closed-loop control policy based on ECAP values, as described above in the second illustrative example, without modifying the waveform of the second stimulation therapy. In this way, IMD 200 is configured to automatically to provide a substantially "smooth" (e.g., low-volatility) sensation of paresthesia for the patient via the first stimulation therapy, while the second stimulation therapy remains unmodulated and serves to, e.g., continuously mediate neuroglial interactions.

In a fourth illustrative example of the independent waveform modulation techniques of this disclosure, IMD 200 concurrently delivers first and second stimulation therapies, having corresponding waveforms similar to those in the first illustrative example (e.g., a first "perceptible" waveform a second "imperceptible" waveform). In this fourth example, in response to determining a triggering condition (e.g., received user input or another condition), IMD 200 is configured to retrieve and implement a corresponding waveform-modulation program 244 that instructs IMD 200 to modulate the first (perceptible) waveform according to both a first modulation technique, and simultaneously, according to a second waveform-modulation technique that is different from the first modulation technique. In other words, the retrieved waveform-modulation program 244 may cause IMD 200 to switch between two or more distinct waveform-modulation techniques for the first (perceptible) waveform in response to monitored values of triggering conditions, without modulating the second (imperceptible) waveform.

For instance, a first waveform-modulation technique may include the closed-loop control policy based on ECAP values as described above in the second illustrative example. The second waveform-modulation technique may include a "positional" waveform-modulation technique based on received sensor (e.g., accelerometer) data, as described in the second illustrative example above.

For example, IMD 200 may monitor the received accelerometer data according to the second "positional" waveform-modulation technique to determine when patient 150 is upright and/or mobile, and to determine when the patient is supine and/or motionless. While the received accelerometer data indicates that patient 150 is in an upright position and/or is mobile, IMD 200 may simultaneously implement the first modulation technique to modulate the first (perceptible) waveform according to the closed-loop control policy based on detected ECAP values. However, when the received accelerometer data indicates that the patient is in a supine position, IMD 200 may apply "open-loop" waveform parameters, in which the first waveform has fixed parameters that are not perceptible by the patient. In such examples, the first waveform may be described as being "partially perceptible" by the patient, in that the patient will experience a substantially consistent sensation of paresthesia while moving, and will experience little-to-no paresthesia while reclining or motionless.

In a fifth illustrative example of the independent-waveform-modulation techniques of this disclosure, IMD 200 concurrently delivers first and second stimulation therapies, having corresponding waveforms similar to those in the first illustrative example (e.g., a first "perceptible" waveform a second "imperceptible" waveform). In this fifth example, in response to determining a triggering condition, IMD 200 retrieves a waveform-modulation program 244 that causes IMD 200 to modulate the first (perceptible) waveform according to a first modulation technique, and to modulate the second (imperceptible) according to a second waveform-modulation technique that is different from the first waveform-modulation technique in at least one respect. For instance, the first waveform-modulation technique may include the closed-loop control policy based on detected ECAP values, as described above in the second illustrative example. The second waveform-modulation technique may include modulation of the current or voltage amplitude of the second (imperceptible) waveform by a sinusoidal carrier wave, e.g., to improve stimulation of wide-dynamic range neurons in the dorsal horn of the brain of the patient.

In a sixth illustrative example of the independent-waveform-modulation techniques of this disclosure, IMD 200 concurrently delivers first and second stimulation therapies, having corresponding waveforms similar to those in the first illustrative example (e.g., a first "perceptible" waveform a second "imperceptible" waveform). In this sixth example, in response to determining a triggering condition such as a "low-battery" indication of power source 224, IMD 200 retrieves a waveform-modulation program 244 that causes IMD 200 to modulate the first (perceptible) waveform according to a first modulation technique, and to modulate the second (imperceptible) waveform according to a second modulation technique (e.g., similar to the fifth illustrative example above). For instance, the first waveform-modulation technique may include the closed-loop control policy based on detected ECAP values, as described above in the second illustrative example. The second waveform-modulation technique may include causing the delivery electrode (s) (e.g., the electrode combination) of the second stimulation therapy to periodically switch between an "active" recharge phase (e.g., an active anodic recharge phase for a cathodic stimulation phase) and a "passive" recharge phase (e.g., a passive anodic recharge phase for a cathodic stimulation phase), e.g., in one-minute increments. The second modulation technique may help to conserve battery capacity for power source 224, e.g., by reducing battery usage during the passive anodic recharge phases, while simultaneously improving or optimizing glutamate release (e.g., via the active anodic recharge pulses) for the patient.

As noted above, these six examples are not intended to be limiting. Other combinations of triggering conditions and corresponding independent-waveform-modulation programs not specifically enumerated above are also contemplated, and may depend on the unique therapeutic needs of each patient.

Figure 6A:
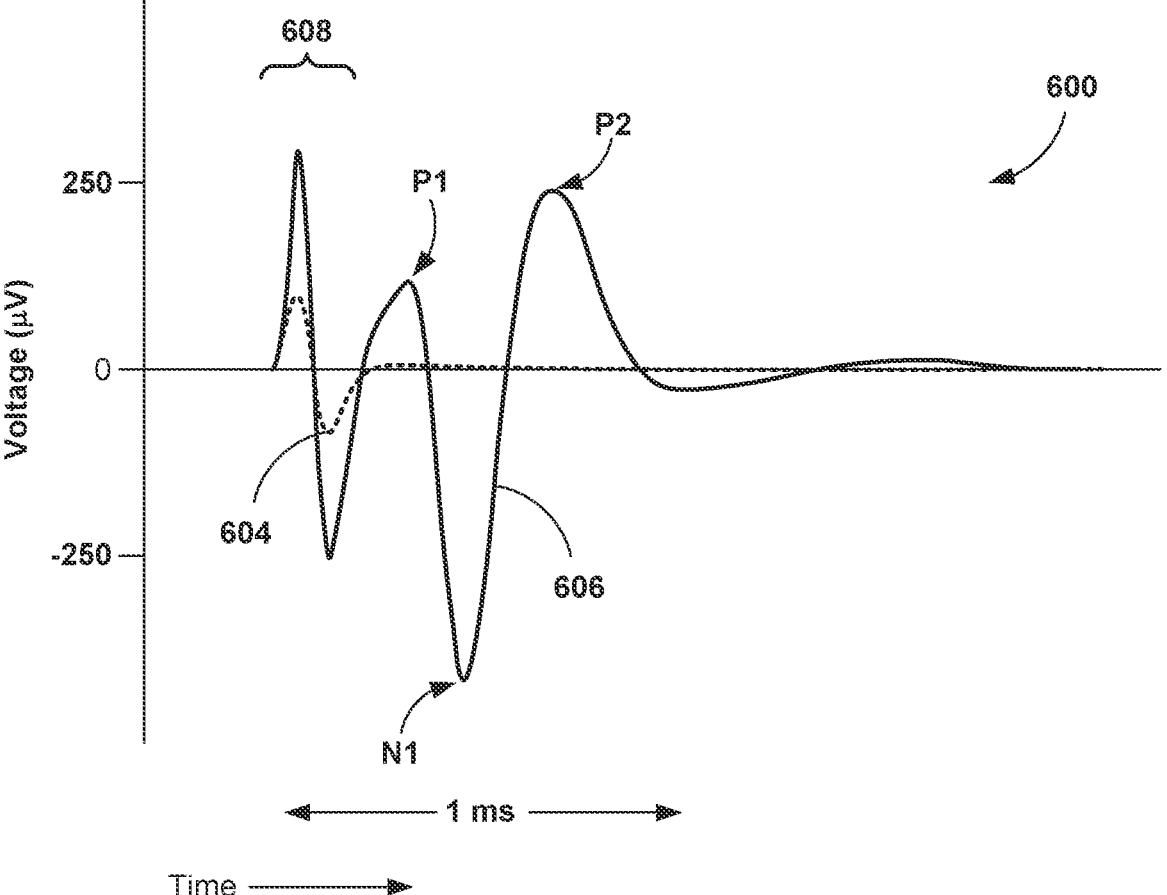
FIG. 6A is a graph of example evoked compound action potentials (ECAPs) sensed for respective stimulation pulses, in accordance with techniques of this disclosure.

FIG. 6A is a graph 600 of example evoked compound action potentials (ECAPs) sensed for respective stimulation pulses, in accordance with one or more techniques of this disclosure. As shown in FIG. 6A, graph 600 shows example ECAP signal 604 (dotted line) and ECAP signal 606 (solid line). In some examples, each of ECAP signals 604 and 606 are sensed from stimulation pulses that were delivered from a guarded cathode, where the control pulses are bi-phasic pulses including an interphase interval between each positive and negative phase of the pulse. In some such examples, the guarded cathode includes stimulation electrodes located at the end of an 8-electrode lead (e.g., leads 130 of FIG. 1) while two sensing electrodes are provided at the other end of the 8-electrode lead. ECAP signal 604 illustrates the voltage amplitude sensed as a result from a sub-detection threshold stimulation pulse. In other words, the stimulation pulse did not elicit a detectable ECAP signal in ECAP signal 604, Peaks 608 of ECAP signal 604 are detected and represent the artifact of the delivered stimulation pulse (e.g., a control pulse that may or may not contribute to a therapeutic effect for the patient). However, no propagating signal is detected after the artifact in ECAP signal 604 because the stimulation pulse was sub-detection threshold (e.g., the intensity of the stimulation pulse was insufficient to cause nerve fibers to depolarize and generate a detectable ECAP signal).

In contrast to ECAP signal 604, ECAP signal 606 represents the voltage amplitude detected from a supra-detection threshold stimulation pulse. Peaks 608 of ECAP signal 606 are detected and represent the artifact of the delivered stimulation pulse. After peaks 408, ECAP signal 606 also includes peaks P1, N1, and P2, which are three typical peaks representative of propagating action potentials from an ECAP. The example duration of the artifact and peaks P1, N1, and P2 is approximately 1 millisecond (ms). The time between two points in the ECAP signal may be referred to as a latency of the ECAP and may indicate the types of fibers being captured by the control pulse. ECAP signals with lower latency (i.e., smaller latency values) indicate a higher percentage of nerve fibers that have faster propagation of signals, whereas ECAP signals with higher latency (i.e., larger latency values) indicate a higher percentage of nerve fibers that have slower propagation of signals. Other characteristics of the ECAP signal may be used in other examples.

The amplitude of the ECAP signal (e.g., peaks within the ECAP signal which may be used as an ECAP characteristic) generally increases with increased amplitude of the stimulation pulse, as long as the pulse amplitude is greater than threshold such that nerves depolarize and propagate the signal. The target ECAP characteristic (e.g., the target ECAP amplitude) may be determined from an ECAP signal associated with an estimated neural response detected from pulses delivering therapy to patient 105. The ECAP signal thus is representative of the distance between the stimulation electrodes and the nerves appropriate for the stimulation parameter values of the pulses delivered at that time.

In some examples, processing circuitry 210 or other devices may be configured to determine a characteristic value for an ECAP signal, for example, from multiple different features of one or more signals associated with the ECAP signal. The characteristic value of the ECAP signal may be determined by removing an artifact from the ECAP signal using the processing circuitry. These different features may be incorporated into an average, weighted average, or other combination that represents the relative action potentials of the ECAP signal. Processing circuitry 210 may determine the characteristic value from different features of the same signal, such as the amplitude difference between two peaks in the ECAP signal and the amplitude difference between two difference peaks in the ECAP signal. As another example of features from the same signal, processing circuitry 210 may determine the characteristic value based on an average of two different peaks in the second derivative signal. Alternatively, processing circuitry 210 may determine the characteristic value of the ECAP signal from features obtained from different signals. For example, processing circuitry 210 may determine the difference between the minimum and maximum values of the first derivative of the ECAP signal on either side of the P2 peak, determine the maximum value of the second derivative of the ECAP signal, and combine each of these factors into a single characteristic value of the ECAP signal. This single characteristic value of the ECAP signal may be referred to as a composite characteristic value because it is a composite of several different factors derived from the ECAP signal in order to obtain a more complete representation of the ECAP signal.

Figure 6B:
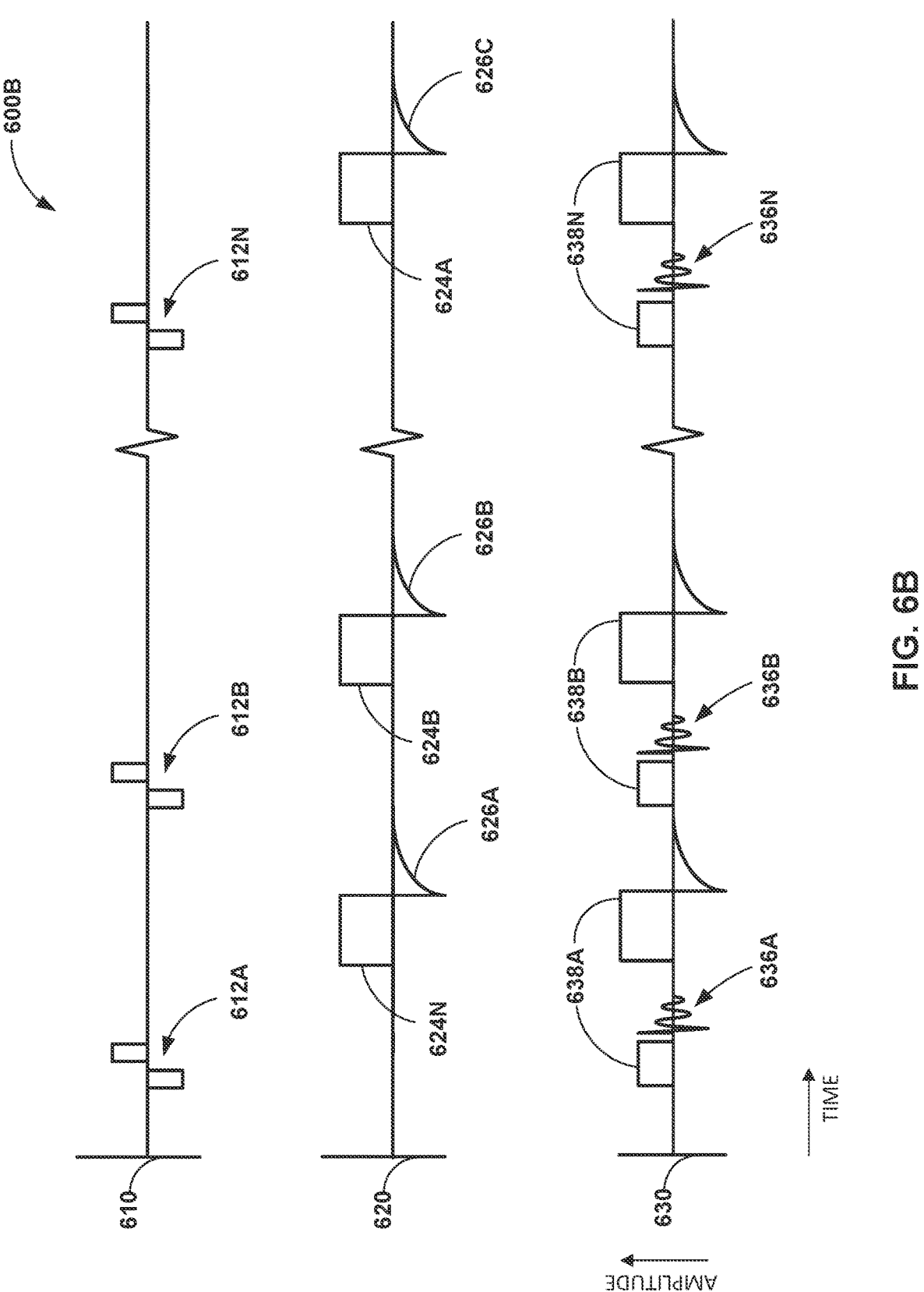
FIG. 6B is a timing diagram illustrating one example of electrical stimulation pulses and respective sensed ECAPs, in accordance with one or more techniques of this disclosure.

FIG. 6B is a timing diagram 602 illustrating one example of electrical stimulation pulses and respective sensed ECAPs, in accordance with one or more techniques of this disclosure. For convenience, FIG. 6B is described with reference to IMD 200 of FIG. 2. As illustrated, timing diagram 602 includes first channel 610, a plurality of control pulses 612A-612N (collectively "control pulses 612"), second channel 620, a plurality of informed pulses 624A-624N (collectively "informed pulses 624") including passive recharge phases 626A-626N (collectively "passive recharge phases 626"), third channel 630, a plurality of respective ECAPs 636A-636N (collectively "ECAPs 636"), and a plurality of stimulation interference signals 638A-638N (collectively "stimulation interference signals 638").

As shown in FIG. 6B, timing diagram 602 provides different trains of pulses that are interleaved over time. Each of the different trains of pulses (e.g., pulses 612 and pulses 624) provide different therapeutic and/or function for therapy, and can be modulated independently as described herein. First channel 610 is a time/voltage (and/or current) graph indicating the voltage (or current) of at least one electrode of electrodes 232, 234. In one example, the stimulation electrodes of first channel 610 may be located on the opposite side of the lead as the sensing electrodes of third channel 630. Control pulses 612 may be electrical pulses delivered to the spinal cord of the patient by at least one of electrodes 232, 234, and control pulses 612 may be balanced biphasic square pulses with an interphase interval. In other words, each of control pulses 612 are shown with a negative phase and a positive phase separated by an interphase interval. For example, a control pulse 612 may have a negative voltage for the same amount of time that it has a positive voltage. It is noted that the negative voltage phase may be before or after the positive voltage phase. In one example, control pulses 612 may have a pulse width of less than approximately 300 microseconds (e.g., the total time of the positive phase, the negative phase, and the interphase interval is less than 300 microseconds). In another example, control pulses 612 may have a pulse width of approximately 100 μs for each phase of the bi-phasic pulse. As illustrated in FIG. 6B, control pulses 612 may be delivered via first channel 610. Delivery of control pulses 612 may be delivered by leads 230 in a guarded cathode electrode combination. For example, if leads 230 are linear 8-electrode leads, a guarded cathode combination is a central cathodic electrode with anodic electrodes immediately adjacent to the cathodic electrode. Control pulses 612 may or may not be perceived by the patient, but are provided to elicit a detectable ECAP signal for use as a feedback control for adjusting some aspect such as informed pulses 624.

Second channel 620 is a time/voltage (and/or current) graph indicating the voltage (or current) of at least one electrode of electrodes 232, 234 for the informed pulses. In one example, the electrodes of second channel 620 may partially or fully share common electrodes with the electrodes of first channel 610 and third channel 630. Informed pulses 624 may also be delivered by the same leads 230 that are configured to deliver control pulses 612. Informed pulses 624 may be interleaved with control pulses 612, such that the two types of pulses are not delivered during overlapping periods of time. However, informed pulses 624 may or may not be delivered by exactly the same electrodes that deliver control pulses 612. Informed pulses 624 may be monophasic pulses with pulse widths of greater than approximately 300 μs and less than approximately 1000 μs. In fact, informed pulses 624 may be configured to have longer pulse widths than control pulses 612. As illustrated in FIG. 6B, informed pulses 624 may be delivered on second channel 620.

Informed pulses 624 may be configured for passive recharge, but could be part of a biphasic or other pulse with active recharge phases. For example, each therapy pulse 624 may be followed by a passive recharge phase 626 to equalize charge on the stimulation electrodes. Unlike a pulse configured for active recharge, where remaining charge on the tissue following a stimulation pulse is instantly removed from the tissue by an opposite applied charge, passive recharge allows tissue to naturally discharge to some reference voltage (e.g., ground or a rail voltage) following the termination of the therapy pulse. In some examples, the electrodes of the medical device may be grounded at the medical device body. In this case, following the termination of therapy pulse 624, the charge on the tissue surrounding the electrodes may dissipate to the medical device, creating a rapid decay of the remaining charge at the tissue following the termination of the pulse. This rapid decay is illustrated in passive recharge phases 626. Passive recharge phase 626 may have a duration in addition to the pulse width of the preceding informed pulse 624. In other examples (not pictured in FIG. 6B), informed pulses 624 may be bi-phasic pulses having a positive and negative phase (and, in some examples, an interphase interval between each phase) which may be referred to as pulses including active recharge. A therapy pulse that is a bi-phasic pulse may or may not have a following passive recharge phase.

Third channel 630 is a time/voltage (and/or current) graph indicating the voltage (or current) of at least one electrode of electrodes 232, 234. In one example, the electrodes of third channel 630 may be located on the opposite side of the lead as the electrodes of first channel 610. ECAPs 636 may be sensed at electrodes 232, 234 from the spinal cord of the patient in response to control pulses 612. ECAPs 636 are electrical signals which may propagate along a nerve away from the origination of control pulses 612. In one example, ECAPs 636 are sensed by different electrodes than the electrodes used to deliver control pulses 612. As illustrated in FIG. 6B, ECAPs 636 may be recorded on third channel 630.

Stimulation interference signals 638A, 638B, and 638N (e.g., the artifact of the stimulation pulses) may be sensed by leads 230 and may be sensed during the same period of time as the delivery of control pulses 612 and informed pulses 624. Since the interference signals may have a greater amplitude and intensity than ECAPs 636, any ECAPs arriving at IMD 200 during the occurrence of stimulation interference signals 638 may not be adequately sensed by sensing circuitry 206 of ID 200. However, ECAPs 636 may be sufficiently sensed by sensing circuitry 206 because each ECAP 636 falls after the completion of each a control pulse 612 and before the delivery of the next therapy pulse 624. As illustrated in FIG. 6B, stimulation interference signals 638 and ECAPs 636 may be recorded on channel 630. In this manner, the system may independently adjust a parameter value of informed pulses 624 based on the sensed ECAP characteristic from the respective ECAP signal. These ECAP-sensing techniques may be used for any ECAP-sensing purpose described herein.

Figure 7:
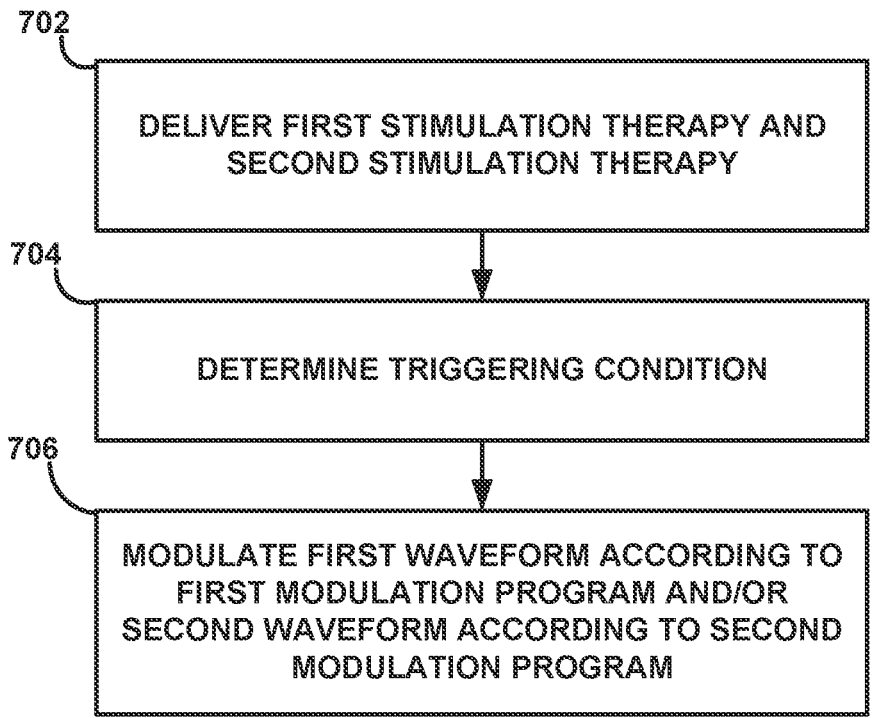
FIG. 7 is a flow diagram illustrating an example technique for independently modulating two or more concurrent electrical stimulation waveforms, in accordance with techniques of this disclosure.

FIG. 7 is a flow diagram illustrating an example technique for independently modulating two or more concurrent stimulation waveforms, in accordance with one or more techniques of this disclosure. IMD 200 and processing circuitry 210 will be described in the example of FIG. 7, but other IMDs such as IMD 110 or other devices (e.g., external programmer 150) or systems may perform, or partially perform, the technique of FIG. 7.

In one or more examples, processing circuitry 210 controls IMD 200 to deliver a plurality of stimulation pulses according to two or more distinct waveforms, e.g., each defined by a periodic pattern of fixed pulse widths, pulse amplitudes, a pulse frequency, etc. (702). In some examples, herein, at least a first waveform of the two or more waveforms may be configured to be perceptible to the patient, e.g., via an evoked sensation of paresthesia, while at least a second waveform of the two or more waveforms may be configured to be substantially imperceptible to the patient. For instance, the second waveform may define an above-threshold pulse frequency at which the patient does not experience paresthesia.

The processing circuitry 210 may also control IMD 200 to determine a triggering condition (704). As used herein, a "triggering condition" may include any set of predetermined criteria, such as, but not limited to, the receipt of sensor data or user input. For instance, sensor data may indicate an amplitude of an ECAP sensed within the patient, accelerometer data indicating a position or movement of the patient, or any other suitable sensor data. The triggering condition may also include the determination or detection of a low-battery capacity indication for IMD 110, or any other similar parameter.

The method may further include modulating, by processing circuitry 210 in response to the triggering condition, either the first (perceptible) waveform, the second (imperceptible) waveform, or both waveforms according to different waveform-modulation programs, or equivalently, according to different waveform-modulation techniques indicated by the a common retrieved waveform-modulation program (706). Non-limiting examples of modulation techniques indicated by waveform-modulation programs include an ECAP-served, closed-loop modulation technique, a sinusoidal carrier wave modulation technique, a periodic on-and-off cycling technique, an active-and-passive anodic recharge cycling technique, a conditional amplitude reduction or deactivation technique, or any other structured waveform-modulation technique defined by objective, programmable criteria.

The following numbered examples illustrate some techniques of this disclosure.

Example 1: In some examples, a medical device system includes: stimulation generation circuitry configured to generate first electrical stimulation and generate second electrical stimulation at least partially concurrent with the first electrical stimulation; and processing circuitry configured to: control the stimulation generation circuitry to deliver the first electrical stimulation to a patient via a first electrode combination, wherein the first electrical stimulation is defined by at least a first set of stimulation parameters selected that the first electrical stimulation exceeds a first perception threshold; control the stimulation generation circuitry to deliver the second electrical stimulation to the patient via a second electrode combination, wherein the second electrical stimulation is defined by at least a second set of stimulation parameters selected that the second electrical stimulation is below a second perception threshold; determine a triggering condition; and responsive to determining the triggering condition, independently modulate one of the first electrical stimulation or the second electrical stimulation.

Example 2: In some examples of the system of example 1, the processing circuitry is configured to independently modulate the first electrical stimulation or the second electrical stimulation by at least modulating the first electrical stimulation according to a first modulation program and modulating the second electrical stimulation according to a second modulation program.

Example 3: In some examples of the system of example 2, the processing circuitry is configured to modulate the second electrical stimulation according to the second modulation program by at least modulating the second electrical stimulation by a sinusoidal carrier wave.

Example 4: In some examples of the system of any of examples 2 or 3, the processing circuitry is configured to modulate the second electrical stimulation according to the second modulation program by at least alternating between an active recharge phase and a passive recharge phase of the second electrode combination.

Example 5: In some examples of the system of example 4, the processing circuitry is configured to alternate between the active recharge phase and the passive recharge phase of the second electrode combination by at least alternating between the active recharge phase and the passive recharge phase of the second electrode combination in one-minute increments.

Example 6: In some examples of the system of any of examples 2 through 5, the processing circuitry is configured to modulate the first electrical stimulation according to the first modulation program by at least adjusting, for each stimulation pulse of a plurality of stimulation pulses of the first electrical stimulation, an amplitude of the stimulation pulse according to a closed-loop control policy based on evoked compound action potential (ECAP) values.

Example 7: In some examples of the system of any of examples 1 through 6, the triggering condition includes one of a presence or an absence of at least one of an electrophysiologic marker, a positional marker, a biochemical marker, or a time-based marker.

Example 8: In some examples of the system of example 7, the triggering condition includes the presence or the absence of the positional marker, the positional marker includes sensor data generated by an accelerometer, and the processing circuitry is configured to determine the triggering condition by determining, based on the sensor data, whether the patient is oriented in an upright position or in a supine position.

Example 9: In some examples of the system of example 8, the processing circuitry is configured to modulate the second electrical stimulation according to the second modulation program by at least: responsive to determining that the patient is in the supine position, suspending the second electrical stimulation; and responsive to determining that the patient is in the upright position, resuming the second electrical stimulation.

Example 10: In some examples of the system of any of examples 1 through 9, the processing circuitry is configured to independently modulate the first electrical stimulation or the second electrical stimulation by at least modulating the first electrical stimulation according to a first modulation program without modulating the second electrical stimulation.

Example 11: In some examples of the system of example 10, the processing circuitry is configured to modulate the first electrical stimulation according to the first modulation program by at least adjusting, for each stimulation pulse of a plurality of stimulation pulses of the first electrical stimulation, an amplitude of the stimulation pulse according to a closed-loop control policy based on evoked compound action potential (ECAP) values.

Example 12: In some examples of the system of any of examples 10 or 11, the processing circuitry is configured to select the second electrode combination to modulate neuro-glial cells.

Example 13: In some examples of the system of any of examples 10 through 12, the processing circuitry is configured to determine the triggering condition by at least determining, based on sensor data, that the patient is mobile; and responsive to determining that the patient is mobile, modulate the first electrical stimulation according to a closed-loop control policy based on ECAP values.

Example 14: In some examples of the system of any of examples 10 through 13, the processing circuitry is configured to determine the triggering condition by at least determining, based on sensor data, that the patient is supine, and wherein the processing circuitry is configured to modulate the first electrical stimulation according to the first modulation program by at least, responsive to determining that the patient is supine, modulating the first electrical stimulation according to an open-loop waveform configuration including fixed, imperceptible waveform parameters.

Example 15: In some examples of the system of example 1, the processing circuitry is configured to independently modulate at least one of the first electrical stimulation or the second electrical stimulation by at least modulating the second stimulation according to a second modulation program without modulating the first electrical stimulation.

Example 16: In some examples of the system of example 15, the processing circuitry is configured to modulate the second electrical stimulation according to the second modulation program by at least cycling an amplitude of the second electrical stimulation through a plurality of different amplitude values.

Example 17: In some examples of the system of example 16, the plurality of different amplitude ranges from about 1 mA to about 0.5 mA.

Example 18: In some examples of the system of any of examples 15 through 17, the processing circuitry is configured to modulate the second electrical stimulation according to the second modulation program by at least modulating the amplitude of the second electrical stimulation at a preselected increment from about 1 minute to about 30 minutes.

Example 19: In some examples of the system of any of examples 15 through 18, the processing circuitry is configured to modulate the second electrical stimulation according to the second modulation program by at least cycling the second electrical stimulation on-and-off.

Example 20: In some examples of the system of any of examples 1 through 19, the first electrical stimulation includes a first train of pulses at least partially interleaved with a second train of pulses of the second electrical stimulation.

Example 21: In some examples of the system of any of examples 1 through 19, the first electrical stimulation includes a first train of pulses; the second electrical stimulation includes a second train of pulses; and one or more pulses of the first train of pulses are delivered simultaneously with one or more pulses of the second train of pulses.

Example 22: In some examples of the system of any of examples 1 through 21, the first electrical stimulation and the second electrical stimulation comprise respective trains of stimulation pulses.

Example 23: In some examples of the system of any of examples 1 through 22, the processing circuitry is configured to independently modulate one of the first electrical stimulation or the second electrical stimulation by at least adjusting a value of one of the first stimulation parameters or the second stimulation parameters.

Example 24: In some examples of the system of any of examples 1 through 23, the first electrical stimulation includes a pulse frequency in a range of about 40 Hz to about 60 Hz.

Example 25: In some examples of the system of any of examples 1 through 24, the first electrical stimulation includes a pulse width of about 200 µs.

Example 26: In some examples of the system of any of examples 1 through 25, the first electrical stimulation is configured to elicit paresthesia in the patient.

Example 27: In some examples of the system of any of examples 1 through 26, the second electrical stimulation includes a pulse frequency of about 10 kdHz.

Example 28: In some examples of the system of any of examples 1 through 26, the second electrical stimulation includes a pulse frequency from about 100 Hz to about 1200 Hz.

Example 29: In some examples of the system of any of examples 1 through 28, the second electrical stimulation includes a pulse width of about 150 µs.

Example 30: In some examples of the system of any of examples 1 through 29, the first electrical stimulation and the second electrical stimulation differ in at least one of: a location of delivery-electrode combination; a stimulation pulse width; a stimulation pulse frequency; a stimulation pulse amplitude; a stimulation-pulse shape; or an interphase interval.

Example 31: In some examples of the system of any of examples 1 through 30, the triggering condition includes at least one of: an indication of a low battery capacity of a battery of the stimulation generation circuitry; an indication of a neurochemical process that is not well-treated by either continuous electrical stimulation or by interrupted electrical stimulation; or detection of a set of parameters indicating an opportunity to improve therapeutic outcomes for the patient by modulating the first waveform or the second waveform.

Example 32: In some examples, a method includes: generating, by stimulation generation circuitry, first electrical stimulation and generate second electrical stimulation at least partially concurrent with the first electrical stimulation; controlling, by processing circuitry, the stimulation generation circuitry to deliver the first electrical stimulation to a patient via a first electrode combination, wherein the first electrical stimulation is defined by at least a first set of stimulation parameters selected that the first electrical stimulation exceeds a first perception threshold; controlling, by the processing circuitry, the stimulation generation circuitry to deliver the second electrical stimulation to the patient via a second electrode combination, wherein the second electrical stimulation is defined by at least a second set of stimulation parameters selected that the second electrical stimulation is below a second perception threshold, determining, by the processing circuitry, a triggering condition; and responsive to determining the triggering condition, independently modulating, by the processing circuitry, one of the first electrical stimulation or the second electrical stimulation.

Example 33: In some examples of the method of example 32, independently modulating the first electrical stimulation or the second electrical stimulation includes at least modulating the first electrical stimulation according to a first modulation program and modulating the second electrical stimulation according to a second modulation program.

Example 34: In some examples of the method of example 33, modulating the second electrical stimulation according to the second modulation program includes at least modulating the second electrical stimulation by a sinusoidal carrier wave.

Example 35: In some examples of the method of any of examples 33 or 34, modulating the second electrical stimulation according to the second modulation program includes alternating between active recharge phase and passive recharge phase of the second electrode combination.

Example 36: In some examples of the method of example 35, alternating between active recharge phase and passive recharge phase of the second electrode combination includes at least alternating between active recharge phase and passive recharge phase of the second electrode combination in one-minute increments.

Example 37: In some examples of the method of any of examples 33 through 36, modulating the first electrical stimulation according to the first modulation program includes at least adjusting, for each stimulation pulse of a plurality of stimulation pulses of the first electrical stimulation, an amplitude of the stimulation pulse according to a closed-loop control policy based on evoked compound action potential (ECAP) values.

Example 38: In some examples of the method of any of examples 32 through 37, the triggering condition includes one of a presence or an absence of at least one of an electrophysiologic marker, a positional marker, a biochemical marker, or a time-based marker.

Example 39: In some examples of the method of example 38, the triggering condition includes the presence or the absence of the positional marker, wherein the positional marker includes sensor data generated by an accelerometer, and determining the triggering condition includes determining, based at least on the sensor data, whether the patient is oriented in an upright position or in a supine position.

Example 40: In some examples of the method of example 39, modulating the second electrical stimulation according to the second modulation program includes at least: responsive to determining that the patient is in the supine position, suspending the second electrical stimulation; and responsive to determining that the patient is in the upright position, resuming the second electrical stimulation.

Example 41: In some examples of the method of any of examples 32 through 40, independently modulating the first electrical stimulation or the second electrical stimulation includes at least modulating the first electrical stimulation according to a first modulation program without modulating the second electrical stimulation.

Example 42: In some examples of the method of example 41, modulating the first electrical stimulation according to the first modulation program includes at least adjusting, for each stimulation pulse of a plurality of stimulation pulses of the first electrical stimulation, an amplitude of the stimulation pulse according to a closed-loop control policy based on evoked compound action potential (ECAP) values.

Example 43: In some examples of the method of any of examples 41 or 42, the method further includes selecting, by the processing circuitry, the second electrode combination to modulate neuroglial cells.

Example 44: In some examples of the method of any of examples 41 through 43, determining the triggering condition includes at least determining, based on sensor data, that the patient is mobile; and responsive to determining that the patient is mobile, modulating the first electrical stimulation according to a closed-loop control policy based on ECAP values.

Example 45: In some examples of the method of any of examples 41 through 43, determining the triggering condition includes at least determining, based on sensor data, that the patient is supine, and modulating the first electrical stimulation according to the first modulation program includes at least, responsive to determining that the patient is supine, modulating the first electrical stimulation according to an open-loop waveform configuration including fixed, imperceptible waveform parameters.

Example 46: In some examples of the method of example 32, independently modulating at least one of the first electrical stimulation or the second electrical stimulation includes at least modulating the second stimulation according to a second modulation program without modulating the first electrical stimulation.

Example 47: In some examples of the method of example 46, modulating the second electrical stimulation according to the second modulation program includes at least cycling an amplitude of the second electrical stimulation through a plurality of different amplitude values.

Example 48. In some examples of the method of example 47, the plurality of different amplitude values ranges from about 1 mA to about 0.5 mA.

Example 49: In some examples of the method of any of examples 46 through 48, modulating the second electrical stimulation according to the second modulation program includes at least modulating the amplitude of the second electrical stimulation at a preselected increment from about 1 minute to about 30 minutes.

Example 50: In some examples of the method of any of examples 46 through 49, modulating the second electrical stimulation according to the second modulation program includes at least cycling the second electrical stimulation on-and-off.

Example 51: In some examples of the method of any of examples 32 through 50, the first electrical stimulation includes a first train of pulses at least partially interleaved with a second train of pulses of the second electrical stimulation.

Example 52: In some examples of the method of any of examples 32 through 50, the first electrical stimulation includes a first train of pulses; the second electrical stimulation includes a second train of pulses; and one or more pulses of the first train of pulses are delivered simultaneously with one or more pulses of the second train of pulses.

Example 53: In some examples of the method of any of examples 32 through 52, the first electrical stimulation and the second electrical stimulation include respective trains of stimulation pulses.

Example 54: In some examples of the method of any of examples 32 through 53, independently modulating one of the first electrical stimulation or the second electrical stimulation includes at least adjusting a value of one of the first stimulation parameters or the second stimulation parameters.

Example 55: In some examples of the method of any of examples 32 through 54, the first electrical stimulation includes a pulse frequency in a range of about 40 Hz to about 60 Hz.

Example 56: In some examples of the method of any of examples 32 through 55, the first electrical stimulation includes a pulse width of about 200 as.

Example 57: In some examples of the method of any of examples 32 through 56, the first electrical stimulation is configured to elicit paresthesia in the patient.

Example 58: In some examples of the method of any of examples 32 through 57, the second electrical stimulation includes a pulse frequency of about 10 kHz.

Example 59: In some examples of the method of any of examples 32 through 57, the second electrical stimulation includes a pulse frequency from about 100 Hz to about 1200 Hz.

Example 60: In some examples of the method of any of examples 32 through 59, the second electrical stimulation includes a pulse width of about 150 μs.

Example 61: In some examples of the method of any of examples 32 through 60, the first electrical stimulation and the second electrical stimulation differ in at least one of: a location of delivery-electrode combination; a stimulation pulse width; a stimulation pulse frequency; a stimulation pulse amplitude; a stimulation-pulse shape; or an interphase interval.

Example 62: In some examples of the method of any of examples 32 through 61, the triggering condition includes at least one of: an indication of a low battery capacity of a battery of the stimulation generation circuitry; an indication of a neurochemical process that is not well-treated by either continuous electrical stimulation or by interrupted electrical stimulation; or detection of a set of parameters indicating an opportunity to improve therapeutic outcomes for the patient by modulating the first waveform or the second waveform.

Example 63: In some examples, a non-transitory, computer-readable medium including instructions that, when executed, cause a processor of a medical device to: control stimulation generation circuitry to deliver first electrical stimulation to a patient via a first electrode combination, wherein the first electrical stimulation is defined by at least a first set of stimulation parameters selected that the first electrical stimulation exceeds a first perception threshold; control the stimulation generation circuitry to deliver second electrical stimulation to the patient via a second electrode combination, wherein the second electrical stimulation is defined by at least a second set of stimulation parameters selected that the second electrical stimulation is below a second perception threshold; determine a triggering condition; and responsive to determining the triggering condition, independently modulate one of the first electrical stimulation or the second electrical stimulation.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. For example, processing circuitry may conduct processing off-line and conduct automatic checks of patient ECAP signals and update programming from a remote location. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer-readable storage media may include random access memory (RAM), ferroelectric random access memory (FRAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

What is claimed is:

1. A medical device system, the system comprising:
an implantable medical device comprising:
stimulation generation circuitry configured to generate first electrical stimulation and generate second electrical stimulation at least partially concurrent with the first electrical stimulation; and
processing circuitry configured to:
control the stimulation generation circuitry to deliver the first electrical stimulation to a patient via a first electrode combination, wherein the first electrical stimulation is defined by at least a first set of stimulation parameters selected that the first electrical stimulation exceeds a first perception threshold;
control the stimulation generation circuitry to deliver the second electrical stimulation to the patient via a second electrode combination, wherein the second electrical stimulation is defined by at least a second set of stimulation parameters selected that the second electrical stimulation is below a second perception threshold;
determine a triggering condition; and
responsive to determining the triggering condition, independently modulate one of the first electrical stimulation or the second electrical stimulation.

2. The system of claim 1, wherein the processing circuitry is configured to independently modulate the first electrical stimulation or the second electrical stimulation by at least modulating the first electrical stimulation according to a first modulation program and modulating the second electrical stimulation according to a second modulation program.

3. The system of claim 2, wherein the processing circuitry is configured to modulate the second electrical stimulation according to the second modulation program by at least modulating the second electrical stimulation by a sinusoidal carrier wave.

4. The system of claim 2, wherein the processing circuitry is configured to modulate the second electrical stimulation according to the second modulation program by at least alternating between an active recharge phase and a passive recharge phase for the second electrode combination.

5. The system of claim 2, wherein the processing circuitry is configured to modulate the first electrical stimulation according to the first modulation program by at least adjusting, for each stimulation pulse of a plurality of stimulation pulses of the first electrical stimulation, an amplitude of the stimulation pulse according to a closed-loop control policy based on evoked compound action potential (ECAP) values.

6. The system of claim 1, wherein the triggering condition comprises one of a presence or an absence of at least one of an electrophysiologic marker, a positional marker, a biochemical marker, or a time-based marker.

7. The system of claim 6, wherein the triggering condition comprises the presence or the absence of the positional marker, wherein the positional marker comprises sensor data generated by an accelerometer, and wherein the processing circuitry is configured to:

determine the triggering condition by determining, based on the sensor data, whether the patient is oriented in an upright position or in a supine position; and modulate the second electrical stimulation according to the second modulation program by at least:

responsive to determining that the patient is in the supine position, suspending the second electrical stimulation; and responsive to determining that the patient is in the upright position, resuming the second electrical stimulation.

8. The system of claim 1, wherein the processing circuitry is configured to modulate the first electrical stimulation according to the first a modulation program by at least adjusting, for each stimulation pulse of a plurality of stimulation pulses of the first electrical stimulation, an amplitude of the stimulation pulse according to a closed-loop control policy based on evoked compound action potential (ECAP) values.

9. The system of claim 1, wherein the processing circuitry is configured to select the second electrode combination to modulate neuroglial cells.

10. The system of claim 1, wherein the processing circuitry is configured to:

determine the triggering condition by at least determining, based on sensor data, that the patient is mobile; and responsive to determining that the patient is mobile, modulate the first electrical stimulation according to a closed-loop control policy based on ECAP values.

11. The system of claim 1, wherein the processing circuitry is configured to modulate the second electrical stimulation according to the second a modulation program by at least cycling an amplitude of the second electrical stimulation through a plurality of different amplitude values.

12. The system of claim 1, wherein the first electrical stimulation comprises a first train of pulses at least partially interleaved with a second train of pulses of the second electrical stimulation.

13. The system of claim 1, wherein the first electrical stimulation comprises a pulse frequency in a range of about 40 Hz to about 60 Hz.

14. The system of claim 1, wherein the second electrical stimulation comprises a pulse frequency from about 100 Hz to about 1200 Hz.

15. A method comprising:

generating, by stimulation generation circuitry of an implantable medical device, first electrical stimulation and generate second electrical stimulation at least partially concurrent with the first electrical stimulation;

controlling, by processing circuitry of the implantable medical device, the stimulation generation circuitry to deliver the first electrical stimulation to a patient via a first electrode combination, wherein the first electrical stimulation is defined by at least a first set of stimulation parameters selected that the first electrical stimulation exceeds a first perception threshold;

controlling, by the processing circuitry of the implantable medical device, the stimulation generation circuitry to deliver the second electrical stimulation to the patient via a second electrode combination, wherein the second electrical stimulation is defined by at least a second set of stimulation parameters selected that the second electrical stimulation is below a second perception threshold;

determining, by the processing circuitry of the implantable medical device, a triggering condition; and responsive to determining the triggering condition, independently modulating, by the processing circuitry of the implantable medical device, one of the first electrical stimulation or the second electrical stimulation.

16. The method of claim 15, wherein independently modulating the first electrical stimulation or the second electrical stimulation comprising at least modulating the first electrical stimulation according to a first modulation program and modulating the second electrical stimulation according to a second modulation program.

17. The method of claim 15, wherein the triggering condition includes one of a presence or an absence of at least one of an electrophysiologic marker, a positional marker, a biochemical marker, or a time-based marker.

18. The method of claim 15, wherein independently modulating the first electrical stimulation or the second electrical stimulation comprises at least modulating the first electrical stimulation according to a first modulation program without modulating the second electrical stimulation.

19. A non-transitory, computer-readable medium comprising instructions that, when executed, cause processing circuitry of an implantable medical device to:

control stimulation generation circuitry of the implantable medical device to deliver first electrical stimulation to a patient via a first electrode combination, wherein the first electrical stimulation is defined by at least a first set of stimulation parameters selected that the first electrical stimulation exceeds a first perception threshold;

control the stimulation generation circuitry to deliver second electrical stimulation to the patient via a second electrode combination, wherein the second electrical stimulation is defined by at least a second set of stimulation parameters selected that the second electrical stimulation is below a second perception threshold;

determine a triggering condition; and responsive to determining the triggering condition, independently modulate one of the first electrical stimulation or the second electrical stimulation.

20. A medical device system, the system comprising:

stimulation generation circuitry configured to generate first electrical stimulation and generate second electrical stimulation at least partially concurrent with the first electrical stimulation; and processing circuitry configured to:

control the stimulation generation circuitry to deliver the first electrical stimulation to a patient via a first electrode combination, wherein the first electrical stimulation is defined by at least a first set of stimulation parameters selected that the first electrical stimulation exceeds a first perception threshold;

control the stimulation generation circuitry to deliver the second electrical stimulation to the patient via a second electrode combination, wherein the second electrical stimulation is defined by at least a second set of stimulation parameters selected that the second electrical stimulation is below a second perception threshold;

determine a triggering condition; and responsive to determining the triggering condition, independently modulate one of the first electrical stimulation or the second electrical stimulation by at least modulating the first electrical stimulation according to a first modulation program and modulating the second electrical stimulation according to a second modulation program.

21. A medical device system, the system comprising:

stimulation generation circuitry configured to generate first electrical stimulation and generate second electrical stimulation at least partially concurrent with the first electrical stimulation, wherein the first electrical stimulation comprises a pulse frequency in a range of about 40 Hz to about 60 Hz; and processing circuitry configured to:

control the stimulation generation circuitry to deliver the first electrical stimulation to a patient via a first electrode combination, wherein the first electrical stimulation is defined by at least a first set of stimulation parameters selected that the first electrical stimulation exceeds a first perception threshold;

control the stimulation generation circuitry to deliver the second electrical stimulation to the patient via a second electrode combination, wherein the second electrical stimulation is defined by at least a second set of stimulation parameters selected that the second electrical stimulation is below a second perception threshold;

determine a triggering condition; and responsive to determining the triggering condition, independently modulate one of the first electrical stimulation or the second electrical stimulation.

22. A medical device system, the system comprising:

stimulation generation circuitry configured to generate first electrical stimulation and generate second electrical stimulation at least partially concurrent with the first electrical stimulation, wherein the second electrical stimulation comprises a pulse frequency from about 100 Hz to about 1200 Hz; and processing circuitry configured to:

control the stimulation generation circuitry to deliver the first electrical stimulation to a patient via a first electrode combination, wherein the first electrical stimulation is defined by at least a first set of stimulation parameters selected that the first electrical stimulation exceeds a first perception threshold;

control the stimulation generation circuitry to deliver the second electrical stimulation to the patient via a second electrode combination, wherein the second electrical stimulation is defined by at least a second set of stimulation parameters selected that the second electrical stimulation is below a second perception threshold;

determine a triggering condition; and responsive to determining the triggering condition, independently modulate one of the first electrical stimulation or the second electrical stimulation.

23. A method comprising:

generating, by stimulation generation circuitry, first electrical stimulation and generate second electrical stimulation at least partially concurrent with the first electrical stimulation;

controlling, by processing circuitry, the stimulation generation circuitry to deliver the first electrical stimulation to a patient via a first electrode combination, wherein the first electrical stimulation is defined by at least a first set of stimulation parameters selected that the first electrical stimulation exceeds a first perception threshold;

controlling, by the processing circuitry, the stimulation generation circuitry to deliver the second electrical stimulation to the patient via a second electrode combination, wherein the second electrical stimulation is defined by at least a second set of stimulation parameters selected that the second electrical stimulation is below a second perception threshold;

determining, by the processing circuitry, a triggering condition; and responsive to determining the triggering condition, independently modulating, by the processing circuitry, one of the first electrical stimulation or the second electrical stimulation by at least modulating the first electrical stimulation according to a first modulation program and modulating the second electrical stimulation according to a second modulation program.

24. A method comprising:

generating, by stimulation generation circuitry, first electrical stimulation and generate second electrical stimulation at least partially concurrent with the first electrical stimulation, wherein the first electrical stimulation comprises a pulse frequency in a range of about 40 Hz to about 60 Hz;

controlling, by processing circuitry, the stimulation generation circuitry to deliver the first electrical stimulation to a patient via a first electrode combination, wherein the first electrical stimulation is defined by at least a first set of stimulation parameters selected that the first electrical stimulation exceeds a first perception threshold;

controlling, by the processing circuitry, the stimulation generation circuitry to deliver the second electrical stimulation to the patient via a second electrode combination, wherein the second electrical stimulation is defined by at least a second set of stimulation parameters selected that the second electrical stimulation is below a second perception threshold;

determining, by the processing circuitry, a triggering condition; and responsive to determining the triggering condition, independently modulating, by the processing circuitry, one of the first electrical stimulation or the second electrical stimulation.

25. A method comprising:

generating, by stimulation generation circuitry, first electrical stimulation and generate second electrical stimulation at least partially concurrent with the first electrical stimulation, wherein the second electrical stimulation comprises a pulse frequency from about 100 Hz to about 1200 Hz;

controlling, by processing circuitry, the stimulation generation circuitry to deliver the first electrical stimulation to a patient via a first electrode combination, wherein the first electrical stimulation is defined by at least a first set of stimulation parameters selected that the first electrical stimulation exceeds a first perception threshold;

controlling, by the processing circuitry, the stimulation generation circuitry to deliver the second electrical stimulation to the patient via a second electrode combination, wherein the second electrical stimulation is defined by at least a second set of stimulation parameters selected that the second electrical stimulation is below a second perception threshold;

determining, by the processing circuitry, a triggering condition; and responsive to determining the triggering condition, independently modulating, by the processing circuitry, one of the first electrical stimulation or the second electrical stimulation.

* * * * *